United States Patent
Lunnen et al.

(10) Patent No.: US 6,958,230 B2
(45) Date of Patent: Oct. 25, 2005

(54) METHOD FOR CLONING AND EXPRESSION OF SBFI RESTRICTION ENDONUCLEASE AND SBFI METHYLASE IN *E. COLI*

(75) Inventors: Keith D. Lunnen, Essex, MA (US); Theodore Davis, Boxford, MA (US); Geoffrey G. Wilson, S. Hamilton, MA (US)

(73) Assignee: New England Biolabs, Inc., Beverly, MA (US)

( * ) Notice: Subject to any disclaimer, the term of this patent is extended or adjusted under 35 U.S.C. 154(b) by 0 days.

(21) Appl. No.: 10/668,047

(22) Filed: Sep. 22, 2003

(65) Prior Publication Data

US 2005/0064433 A1 Mar. 24, 2005

(51) Int. Cl.[7] ............................. C12N 9/22; C12N 15/55
(52) U.S. Cl. ................. 435/199; 435/320.1; 435/252.3; 536/23.2
(58) Field of Search ............................. 435/199, 252.3, 435/320.1; 536/23.2

(56) References Cited

U.S. PATENT DOCUMENTS 5,098,839 A    3/1992  Polisson
5,200,333 A    4/1993  Wilson

OTHER PUBLICATIONS

Roberts et al., Nucl. Acids Res. 29: 268–269 (2001).
Hopwood et al., Genetic Manipulation of Streptomyces: A Laboratory Manual. John Innes Foundation, Norwich, p. 77 (1985).

*Primary Examiner*—James Ketter
*Assistant Examiner*—Nancy T. Vogel
(74) *Attorney, Agent, or Firm*—Harriet M. Strimpel; Gregory D. Williams

(57) ABSTRACT

The present invention relates to: recombinant DNA encoding the SbfI restriction endonuclease as well as the SbfI methylase, and expression of the SbfI restriction endonuclease and SbfI methylase in *E. coli* cells containing the recombinant DNA; and methods for cloning the SbfI restriction gene (sbfIR) from *Streptomyces* species Bf-61 into *E. coli* by PCR. The method relied on primers based on DNA sequences predicted from amino acid sequences of the purified SbfI restriction endonuclease.

6 Claims, 9 Drawing Sheets

Figure 2-1

```
       GTGCATCCGATCGCCAGCACTGAAACTCGCCGCCAAGCTGCTCTCGGCAAACTGGACCCC
  1    ---------+---------+---------+---------+---------+---------+   60
       M  H  P  I  A  S  T  E  T  R  R  Q  A  A  L  G  K  L  D  P
       ACTACTCAAGCGGTGCTAGGGCAGTTCTTCACTCCCATGAAGGCCGCCACGCTGATGGCT
  61   ---------+---------+---------+---------+---------+---------+   120
       T  T  Q  A  V  L  G  Q  F  F  T  P  M  K  A  A  T  L  M  A
       TCAATGCTTCGGGTCGATGATCTCCGCGGAACGGTGCGGGTGCTCGACCCAGGAGCTGGT
 121   ---------+---------+---------+---------+---------+---------+   180
       S  M  L  R  V  D  D  L  R  G  T  V  R  V  L  D  P  G  A  G
       GTCGGGTCTCTGACCGCTGCCCTCGTCGATCGGCTGCATACTGAACGCCCCGACGTTGCG
 181   ---------+---------+---------+---------+---------+---------+   240
       V  G  S  L  T  A  A  L  V  D  R  L  H  T  E  R  P  D  V  A
       GTCCACGTAGTTGCCGTGGAAACCGACCCCTTTGTCGTGCCTTACCTGCGCGCCACCCTG
 241   ---------+---------+---------+---------+---------+---------+   300
       V  H  V  V  A  V  E  T  D  P  F  V  V  P  Y  L  R  A  T  L
       GAGGAATGTCGGAACGCTTACGGCATCTCCTACGACCTAGTCGAGGGCGACTATTTGCTT
 301   ---------+---------+---------+---------+---------+---------+   360
       E  E  C  R  N  A  Y  G  I  S  Y  D  L  V  E  G  D  Y  L  L
       AACCAAGGGGCCAAGCTGGATGGCCCGTTCGATCTTGTAATTGCTAATCCTCCCTACGGA
 361   ---------+---------+---------+---------+---------+---------+   420
       N  Q  G  A  K  L  D  G  P  F  D  L  V  I  A  N  P  P  Y  G
       AAGCTTGCTTCAGATTCGCTGGCGCGGCTTGCAACGACAGCGCGTGCCGTCGATGTACCG
 421   ---------+---------+---------+---------+---------+---------+   480
       K  L  A  S  D  S  L  A  R  L  A  T  T  A  R  A  V  D  V  P
       AACGTTTACGTGGCCTTCTGGGTGCGAGCAGTCATTTCGCTCAAAGAGCAGGGGCGGGGG
 481   ---------+---------+---------+---------+---------+---------+   540
       N  V  Y  V  A  F  W  V  R  A  V  I  S  L  K  E  Q  G  R  G
       GTTTTCATTGTTCCTCGATCTTGGGCGAACGGGCCTTACTATCGTCAATTTCGCCATTGG
 541   ---------+---------+---------+---------+---------+---------+   600
       V  F  I  V  P  R  S  W  A  N  G  P  Y  Y  R  Q  F  R  H  W
       CTGATGACCGCGGTAAGTCTCGATATACTTCATGTGTTCGAAAGTAGAACCAAAGTATTT
 601   ---------+---------+---------+---------+---------+---------+   660
       L  M  T  A  V  S  L  D  I  L  H  V  F  E  S  R  T  K  V  F
       GCGGACACGAAGGTAAAGCAAGAGAATGTCATCGTTGCTTTCAGTGTGAGGCCGCAAAGC
 661   ---------+---------+---------+---------+---------+---------+   720
       A  D  T  K  V  K  Q  E  N  V  I  V  A  F  S  V  R  P  Q  S
       TCTAGTGTGGTCCTTTCTAGGTCGGTCGCACATGGAGAAGAGTCGATCGCAAGTTCTGTG
 721   ---------+---------+---------+---------+---------+---------+   780
       S  S  V  V  L  S  R  S  V  A  H  G  E  E  S  I  A  S  S  V
       CCGTTTTCTGCGCTTGTTCATGATGAAGACGATGACAAAATCGTGCACTTCGCGGAAAGC
 781   ---------+---------+---------+---------+---------+---------+   840
       P  F  S  A  L  V  H  D  E  D  D  D  K  I  V  H  F  A  E  S
       GCATCGGTGCCCTCGGCGGCGAGGTTTACTCTCGCTGATCTCGGCATCGGTGTAAGTACG
 841   ---------+---------+---------+---------+---------+---------+   900
       A  S  V  P  S  A  A  R  F  T  L  A  D  L  G  I  G  V  S  T
       GGAAAGGTTGTTGATTTTCGCAATCGTCAGTATTTGACCGATAACCTGGATGCTTCAGGC
 901   ---------+---------+---------+---------+---------+---------+   960
       G  K  V  V  D  F  R  N  R  Q  Y  L  T  D  N  L  D  A  S  G
       GTTGTGCCCATGGTTTATCAGTCAAACATTCGATCTGGTAAAATTGATTGGCCTCAGGTG
 961   ---------+---------+---------+---------+---------+---------+   1020
       V  V  P  M  V  Y  Q  S  N  I  R  S  G  K  I  D  W  P  Q  V
       GGTGCGAGGAAGCCTCAAGGATTTGTTGCGGTCGAAGATGTAGCACTACGTCAACTTCTC
 1021  ---------+---------+---------+---------+---------+---------+   1080
       G  A  R  K  P  Q  G  F  V  A  V  E  D  V  A  L  R  Q  L  L
```

Figure 2-2

```
      CCGCAAGGGTCGTATGTTGTTGTGAAACGGCAAACGGCGAAAGAGGACCGTCGTCGTGTC
1081  ---------+---------+---------+---------+---------+---------+  1140
      P  Q  G  S  Y  V  V  V  K  R  Q  T  A  K  E  D  R  R  R  V
      ATCGCTGCGGTCTGGGACGGGGCCAGCAGGGTTGCGCTCGACAATAAAACGAACTATTTG
1141  ---------+---------+---------+---------+---------+---------+  1200
      I  A  A  V  W  D  G  A  S  R  V  A  L  D  N  K  T  N  Y  L
      CATGAATCTCAACGACCGCTTGAGAAAAATGTGGCCCGCGGCCTCATGCTTTGGTTGAAC
1201  ---------+---------+---------+---------+---------+---------+  1260
      H  E  S  Q  R  P  L  E  K  N  V  A  R  G  L  M  L  W  L  N
      TCGACTGTGTTGGATCAGTATTTCCGAGCCTTTTCCGGGCATACCCAGGTGAACGCTGGC
1261  ---------+---------+---------+---------+---------+---------+  1320
      S  T  V  L  D  Q  Y  F  R  A  F  S  G  H  T  Q  V  N  A  G
      GATCTACGCCGGCTTCCGTTCCTCTGTCGCGAGGACCTAATTCTTCTCGCTAAGGTCGTT
1321  ---------+---------+---------+---------+---------+---------+  1380
      D  L  R  R  L  P  F  L  C  R  E  D  L  I  L  L  A  K  V  V
      CCCGATGGCCTGCCTGATCAGGAGACGTTGGATGCCGTGGTGGCCAGACTCTTCTGTGAG
1381  ---------+---------+---------+---------+---------+---------+  1440
      P  D  G  L  P  D  Q  E  T  L  D  A  V  V  A  R  L  F  C  E
      ATTCCGGAATCTGCCTCGTGA
1441  ---------+---------+-  1461
      I  P  E  S  A  S  *
```

Figure 3

```
     GTGAACAGCAGTGACGGCATCGACGGAACGGTAGCGAGCATCGATACTGCGCGGGCGCTG
  1  ------------------------------------------------------------+  60
     M  N  S  S  D  G  I  D  G  T  V  A  S  I  D  T  A  R  A  L
     CTAAAGCGTTTTGGGTTTGACGCGCAACGATATAACGTCCGTAGCGCTGTGACATTGCTC
 61  ------------------------------------------------------------+ 120
     L  K  R  F  G  F  D  A  Q  R  Y  N  V  R  S  A  V  T  L  L
     GCGCTTGCCGGTTTGAAGCCGGGAGATCGCTGGGTTGACTCGACCACTCCACGCCTTGGC
121  ------------------------------------------------------------+ 180
     A  L  A  G  L  K  P  G  D  R  W  V  D  S  T  T  P  R  L  G
     GTTCAGAAGATCATGGACTGGTCCGGCGAGCATTGGGCCAAGCCGTACGCCACCGGAAGT
181  ------------------------------------------------------------+ 240
     V  Q  K  I  M  D  W  S  G  E  H  W  A  K  P  Y  A  T  G  S
     CGAGAAGATTTCCGTAAGAAGACGCTTCGGCAGTGGGTTGATAATGGCTTCGCCGTACTT
241  ------------------------------------------------------------+ 300
     R  E  D  F  R  K  K  T  L  R  Q  W  V  D  N  G  F  A  V  L
     AATGCGGACAATTTAAACATCGCCACGAACTCGCAGCTCAACGAGTACTGCTTGTCTGAC
301  ------------------------------------------------------------+ 360
     N  A  D  N  L  N  I  A  T  N  S  Q  L  N  E  Y  C  L  S  D
     GAAGCATTACAGGCGCTAAGGGCATATGGAACGGAAGGCTTCGAGGAATCTCTTGTAGTC
361  ------------------------------------------------------------+ 420
     E  A  L  Q  A  L  R  A  Y  G  T  E  G  F  E  E  S  L  V  V
     TTTCTTGATGAAGCATCGAAGGCGGTTAAAGCGCGAGCGGAAGCTCTCCAGGCTGCGATG
421  ------------------------------------------------------------+ 480
     F  L  D  E  A  S  K  A  V  K  A  R  A  E  A  L  Q  A  A  M
     ATCTCTGTCGATCTCCCTGGTGGCGAGGAATTTCTGCTCTCGCCTGCCGGGCAGAATCCA
481  ------------------------------------------------------------+ 540
     I  S  V  D  L  P  G  G  E  E  F  L  L  S  P  A  G  Q  N  P
     TTGCTGAAGAAGATGGTCGAAGAGTTTGTGCCGCGATTTGCACCTCGCTCGACGGTGCTC
541  ------------------------------------------------------------+ 600
     L  L  K  K  M  V  E  E  F  V  P  R  F  A  P  R  S  T  V  L
     TACCTCGGGGATACTCGTGGAAAGCATTCCCTATTCGAACGAGAGATCTTTGAAGAGGTG
601  ------------------------------------------------------------+ 660
     Y  L  G  D  T  R  G  K  H  S  L  F  E  R  E  I  F  E  E  V
     CTCGGCCTGACTTTCGACCCCCATGGTCGAATGCCGGACCTTATTCTCCATGACGAAGTT
661  ------------------------------------------------------------+ 720
     L  G  L  T  F  D  P  H  G  R  M  P  D  L  I  L  H  D  E  V
     CGTGGGTGGCTTTTCCTTATGGAGGCCGTGAAAAGTAAAGGTCCGTTTGATGAGGAGCGG
721  ------------------------------------------------------------+ 780
     R  G  W  L  F  L  M  E  A  V  K  S  K  G  P  F  D  E  E  R
     CATCGCAGCCTGCAAGAGCTATTCGTTACACCTTCAGCGGGTCTAATTTTTGTAAACTGC
781  ------------------------------------------------------------+ 840
     H  R  S  L  Q  E  L  F  V  T  P  S  A  G  L  I  F  V  N  C
     TTTGAAAATCGTGAGTCGATGCGTCAGTGGCTCCCTGAGCTGGCTTGGGAAACTGAGGCG
841  ------------------------------------------------------------+ 900
     F  E  N  R  E  S  M  R  Q  W  L  P  E  L  A  W  E  T  E  A
     TGGGTAGCGGAAGATCCAGACCATCTGATTCACCTTAACGGGTCTAGATTTCTTGGGCCG
901  ------------------------------------------------------------+ 960
     W  V  A  E  D  P  D  H  L  I  H  L  N  G  S  R  F  L  G  P
     TACGAACGTTAG
961  ------------+-- 972
     Y  E  R  *
```

Fig. 4 pstIM-pACYC184
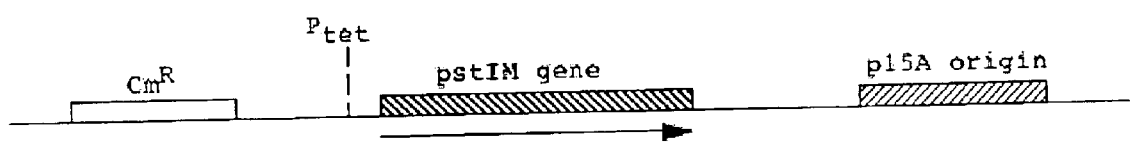

Fig. 5 sbfIM-pACYC184
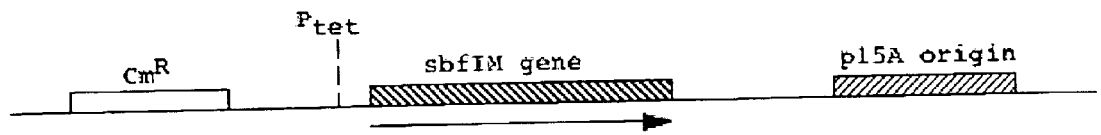

Fig. 6 pCAB16
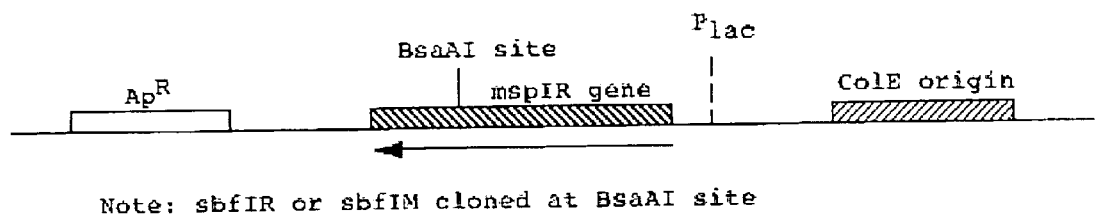
Note: sbfIR or sbfIM cloned at BsaAI site

Fig. 7  sbfIR-pLT7K
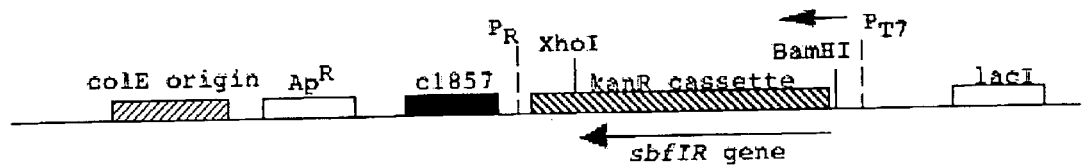
Note: sbfIR cloned at BamHI to XhoI site

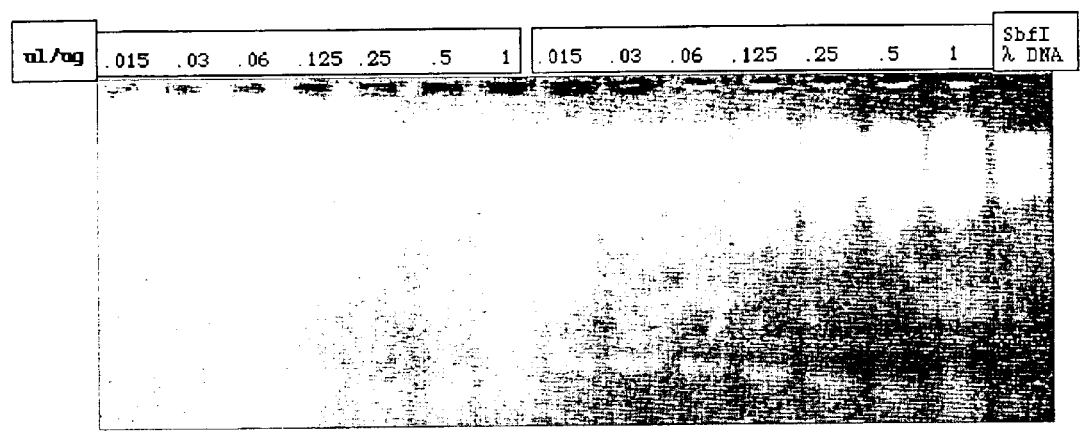
Fig 8 Final Overexpression of SbfI Endonuclease
NEB#1500, ER2848 [pACYC184-SbfIM #7, pLT7K-SbfIR #12]

ization, as molecular tools for gene

SEQUENCE LISTING

<160> NUMBER OF SEQ ID NOS: 57

<210> SEQ ID NO 1
<211> LENGTH: 1461
<212> TYPE: DNA
<213> ORGANISM: streptomyces species Bf-61
<220> FEATURE:
<221> NAME/KEY: CDS
<222> LOCATION: (1)..(1461)

<400> SEQUENCE: 1

```
gtg cat ccg atc gcc agc act gaa act cgc cgc caa gct gct ctc ggc      48
Met His Pro Ile Ala Ser Thr Glu Thr Arg Arg Gln Ala Ala Leu Gly
1               5                  10                  15 aaa ctg gac ccc act act caa gcg gtg cta ggg cag ttc ttc act ccc      96
Lys Leu Asp Pro Thr Thr Gln Ala Val Leu Gly Gln Phe Phe Thr Pro
            20                  25                  30 atg aag gcc gcc acg ctg atg gct tca atg ctt cgg gtc gat gat ctc     144
Met Lys Ala Ala Thr Leu Met Ala Ser Met Leu Arg Val Asp Asp Leu
        35                  40                  45 cgc gga acg gtg cgg gtg ctc gac cca gga gct ggt gtc ggg tct ctg     192
Arg Gly Thr Val Arg Val Leu Asp Pro Gly Ala Gly Val Gly Ser Leu
    50                  55                  60 acc gct gcc ctc gtc gat cgg ctg cat act gaa cgc ccc gac gtt gcg     240
Thr Ala Ala Leu Val Asp Arg Leu His Thr Glu Arg Pro Asp Val Ala
65                  70                  75                  80 gtc cac gta gtt gcc gtg gaa acc gac ccc ttt gtc gtg cct tac ctg     288
```

-continued

| | | | | | | | | | | | | | | | |
|---|---|---|---|---|---|---|---|---|---|---|---|---|---|---|---|
| Val | His | Val | Val | Ala | Val | Glu | Thr | Asp | Pro | Phe | Val | Pro | Tyr | Leu | |
| | | | 85 | | | | | 90 | | | | 95 | | | |

```
cgc gcc acc ctg gag gaa tgt cgg aac gct tac ggc atc tcc tac gac      336
Arg Ala Thr Leu Glu Glu Cys Arg Asn Ala Tyr Gly Ile Ser Tyr Asp
            100                 105                 110 cta gtc gag ggc gac tat ttg ctt aac caa ggg gcc aag ctg gat ggc      384
Leu Val Glu Gly Asp Tyr Leu Leu Asn Gln Gly Ala Lys Leu Asp Gly
            115                 120                 125 ccg ttc gat ctt gta att gct aat cct ccc tac gga aag ctt gct tca      432
Pro Phe Asp Leu Val Ile Ala Asn Pro Pro Tyr Gly Lys Leu Ala Ser
130             135                 140 gat tcg ctg gcg cgg ctt gca acg aca gcg cgt gcc gtc gat gta ccg      480
Asp Ser Leu Ala Arg Leu Ala Thr Thr Ala Arg Ala Val Asp Val Pro
145             150                 155                 160 aac gtt tac gtg gcc ttc tgg gtg cga gca gtc att tcg ctc aaa gag      528
Asn Val Tyr Val Ala Phe Trp Val Arg Ala Val Ile Ser Leu Lys Glu
                165                 170                 175 cag ggg cgg ggg gtt ttc att gtt cct cga tct tgg gcg aac ggg cct      576
Gln Gly Arg Gly Val Phe Ile Val Pro Arg Ser Trp Ala Asn Gly Pro
            180                 185                 190 tac tat cgt caa ttt cgc cat tgg ctg atg acc gcg gta agt ctc gat      624
Tyr Tyr Arg Gln Phe Arg His Trp Leu Met Thr Ala Val Ser Leu Asp
            195                 200                 205 ata ctt cat gtg ttc gaa agt aga acc aaa gta ttt gcg gac acg aag      672
Ile Leu His Val Phe Glu Ser Arg Thr Lys Val Phe Ala Asp Thr Lys
210             215                 220 gta aag caa gag aat gtc atc gtt gct ttc agt gtg agg ccg caa agc      720
Val Lys Gln Glu Asn Val Ile Val Ala Phe Ser Val Arg Pro Gln Ser
225             230                 235                 240 tct agt gtg gtc ctt tct agg tcg gtc gca cat gga gaa gag tcg atc      768
Ser Ser Val Val Leu Ser Arg Ser Val Ala His Gly Glu Glu Ser Ile
                245                 250                 255 gca agt tct gtg ccg ttt tct gcg ctt gtt cat gat gaa gac gat gac      816
Ala Ser Ser Val Pro Phe Ser Ala Leu Val His Asp Glu Asp Asp Asp
            260                 265                 270 aaa atc gtg cac ttc gcg gaa agc gca tcg gtg ccc tcg gcg gcg agg      864
Lys Ile Val His Phe Ala Glu Ser Ala Ser Val Pro Ser Ala Ala Arg
            275                 280                 285 ttt act ctc gct gat ctc ggc atc ggt gta agt acg gga aag gtt gtt      912
Phe Thr Leu Ala Asp Leu Gly Ile Gly Val Ser Thr Gly Lys Val Val
            290                 295                 300 gat ttt cgc aat cgt cag tat ttg acc gat aac ctg gat gct tca ggc      960
Asp Phe Arg Asn Arg Gln Tyr Leu Thr Asp Asn Leu Asp Ala Ser Gly
305             310                 315                 320 gtt gtg ccc atg gtt tat cag tca aac att cga tct ggt aaa att gat     1008
Val Val Pro Met Val Tyr Gln Ser Asn Ile Arg Ser Gly Lys Ile Asp
                325                 330                 335 tgg cct cag gtg ggt gcg agg aag cct caa gga ttt gtt gcg gtc gaa     1056
Trp Pro Gln Val Gly Ala Arg Lys Pro Gln Gly Phe Val Ala Val Glu
            340                 345                 350 gat gta gca cta cgt caa ctt ctc ccg caa ggg tcg tat gtt gtt gtg     1104
Asp Val Ala Leu Arg Gln Leu Leu Pro Gln Gly Ser Tyr Val Val Val
            355                 360                 365 aaa cgg caa acg gcg aaa gag gac cgt cgt cgt gtc atc gct gcg gtc     1152
Lys Arg Gln Thr Ala Lys Glu Asp Arg Arg Arg Val Ile Ala Ala Val
370             375                 380 tgg gac ggg gcc agc agg gtt gcg ctc gac aat aaa acg aac tat ttg     1200
Trp Asp Gly Ala Ser Arg Val Ala Leu Asp Asn Lys Thr Asn Tyr Leu
385             390                 395                 400
```

```
cat gaa tct caa cga ccg ctt gag aaa aat gtg gcc cgc ggc ctc atg    1248
His Glu Ser Gln Arg Pro Leu Glu Lys Asn Val Ala Arg Gly Leu Met
                405                 410                 415 ctt tgg ttg aac tcg act gtg ttg gat cag tat ttc cga gcc ttt tcc    1296
Leu Trp Leu Asn Ser Thr Val Leu Asp Gln Tyr Phe Arg Ala Phe Ser
            420                 425                 430 ggg cat acc cag gtg aac gct ggc gat cta cgc cgg ctt ccg ttc ctc    1344
Gly His Thr Gln Val Asn Ala Gly Asp Leu Arg Arg Leu Pro Phe Leu
        435                 440                 445 tgt cgc gag gac cta att ctt ctc gct aag gtc gtt ccc gat ggc ctg    1392
Cys Arg Glu Asp Leu Ile Leu Leu Ala Lys Val Val Pro Asp Gly Leu
    450                 455                 460 cct gat cag gag acg ttg gat gcc gtg gtg gcc aga ctc ttc tgt gag    1440
Pro Asp Gln Glu Thr Leu Asp Ala Val Val Ala Arg Leu Phe Cys Glu
465                 470                 475                 480 att ccg gaa tct gcc tcg tga                                        1461
Ile Pro Glu Ser Ala Ser
                485

<210> SEQ ID NO 2
<211> LENGTH: 486
<212> TYPE: PRT
<213> ORGANISM: streptomyces species Bf-61

<400> SEQUENCE: 2

Met His Pro Ile Ala Ser Thr Glu Thr Arg Arg Gln Ala Ala Leu Gly
1               5                   10                  15

Lys Leu Asp Pro Thr Thr Gln Ala Val Leu Gly Gln Phe Phe Thr Pro
            20                  25                  30

Met Lys Ala Ala Thr Leu Met Ala Ser Met Leu Arg Val Asp Asp Leu
        35                  40                  45

Arg Gly Thr Val Arg Val Leu Asp Pro Gly Ala Gly Val Gly Ser Leu
    50                  55                  60

Thr Ala Ala Leu Val Asp Arg Leu His Thr Glu Arg Pro Asp Val Ala
65                  70                  75                  80

Val His Val Val Ala Val Glu Thr Asp Pro Phe Val Val Pro Tyr Leu
                85                  90                  95

Arg Ala Thr Leu Glu Glu Cys Arg Asn Ala Tyr Gly Ile Ser Tyr Asp
            100                 105                 110

Leu Val Glu Gly Asp Tyr Leu Leu Asn Gln Gly Ala Lys Leu Asp Gly
        115                 120                 125

Pro Phe Asp Leu Val Ile Ala Asn Pro Pro Tyr Gly Lys Leu Ala Ser
    130                 135                 140

Asp Ser Leu Ala Arg Leu Ala Thr Thr Ala Arg Ala Val Asp Val Pro
145                 150                 155                 160

Asn Val Tyr Val Ala Phe Trp Val Arg Ala Val Ile Ser Leu Lys Glu
                165                 170                 175

Gln Gly Arg Gly Val Phe Ile Val Pro Arg Ser Trp Ala Asn Gly Pro
            180                 185                 190

Tyr Tyr Arg Gln Phe Arg His Trp Leu Met Thr Ala Val Ser Leu Asp
        195                 200                 205

Ile Leu His Val Phe Glu Ser Arg Thr Lys Val Phe Ala Asp Thr Lys
    210                 215                 220

Val Lys Gln Glu Asn Val Ile Val Ala Phe Ser Val Arg Pro Gln Ser
225                 230                 235                 240

Ser Ser Val Val Leu Ser Arg Ser Val Ala His Gly Glu Glu Ser Ile
                245                 250                 255
```

```
Ala Ser Ser Val Pro Phe Ser Ala Leu Val His Asp Glu Asp Asp
        260                 265                 270

Lys Ile Val His Phe Ala Glu Ser Ala Ser Val Pro Ser Ala Ala Arg
        275                 280                 285

Phe Thr Leu Ala Asp Leu Gly Ile Gly Val Ser Thr Gly Lys Val Val
        290                 295                 300

Asp Phe Arg Asn Arg Gln Tyr Leu Thr Asp Asn Leu Asp Ala Ser Gly
305                 310                 315                 320

Val Val Pro Met Val Tyr Gln Ser Asn Ile Arg Ser Gly Lys Ile Asp
                325                 330                 335

Trp Pro Gln Val Gly Ala Arg Lys Pro Gln Gly Phe Val Ala Val Glu
        340                 345                 350

Asp Val Ala Leu Arg Gln Leu Leu Pro Gln Gly Ser Tyr Val Val Val
            355                 360                 365

Lys Arg Gln Thr Ala Lys Glu Asp Arg Arg Val Ile Ala Ala Val
        370                 375                 380

Trp Asp Gly Ala Ser Arg Val Ala Leu Asp Asn Lys Thr Asn Tyr Leu
385                 390                 395                 400

His Glu Ser Gln Arg Pro Leu Glu Lys Asn Val Ala Arg Gly Leu Met
                405                 410                 415

Leu Trp Leu Asn Ser Thr Val Leu Asp Gln Tyr Phe Arg Ala Phe Ser
                420                 425                 430

Gly His Thr Gln Val Asn Ala Gly Asp Leu Arg Arg Leu Pro Phe Leu
            435                 440                 445

Cys Arg Glu Asp Leu Ile Leu Leu Ala Lys Val Val Pro Asp Gly Leu
        450                 455                 460

Pro Asp Gln Glu Thr Leu Asp Ala Val Val Ala Arg Leu Phe Cys Glu
465                 470                 475                 480

Ile Pro Glu Ser Ala Ser
                485

<210> SEQ ID NO 3
<211> LENGTH: 972
<212> TYPE: DNA
<213> ORGANISM: streptomyces species Bf-61
<220> FEATURE:
<221> NAME/KEY: CDS
<222> LOCATION: (1)..(972)

<400> SEQUENCE: 3 gtg aac agc agt gac ggc atc gac gga acg gta gcg agc atc gat act     48
Met Asn Ser Ser Asp Gly Ile Asp Gly Thr Val Ala Ser Ile Asp Thr
1               5                   10                  15 gcg cgg gcg ctg cta aag cgt ttt ggg ttt gac gcg caa cga tat aac     96
Ala Arg Ala Leu Leu Lys Arg Phe Gly Phe Asp Ala Gln Arg Tyr Asn
            20                  25                  30 gtc cgt agc gct gtg aca ttg ctc gcg ctt gcc ggt ttg aag ccg gga    144
Val Arg Ser Ala Val Thr Leu Leu Ala Leu Ala Gly Leu Lys Pro Gly
        35                  40                  45 gat cgc tgg gtt gac tcg acc act cca cgc ctt ggc gtt cag aag atc    192
Asp Arg Trp Val Asp Ser Thr Thr Pro Arg Leu Gly Val Gln Lys Ile
    50                  55                  60 atg gac tgg tcc ggc gag cat tgg gcc aag ccg tac gcc acc gga agt    240
Met Asp Trp Ser Gly Glu His Trp Ala Lys Pro Tyr Ala Thr Gly Ser
65                  70                  75                  80 cga gaa gat ttc cgt aag aag acg ctt cgg cag tgg gtt gat aat ggc    288
Arg Glu Asp Phe Arg Lys Lys Thr Leu Arg Gln Trp Val Asp Asn Gly
```

```
                85                  90                  95
ttc gcc gta ctt aat gcg gac aat tta aac atc gcc acg aac tcg cag       336
Phe Ala Val Leu Asn Ala Asp Asn Leu Asn Ile Ala Thr Asn Ser Gln
            100                 105                 110 ctc aac gag tac tgc ttg tct gac gaa gca tta cag gcg cta agg gca       384
Leu Asn Glu Tyr Cys Leu Ser Asp Glu Ala Leu Gln Ala Leu Arg Ala
            115                 120                 125 tat gga acg gaa ggc ttc gag gaa tct ctt gta gtc ttt ctt gat gaa       432
Tyr Gly Thr Glu Gly Phe Glu Glu Ser Leu Val Val Phe Leu Asp Glu
    130                 135                 140 gca tcg aag gcg gtt aaa gcg cga gcg gaa gct ctc cag gct gcg atg       480
Ala Ser Lys Ala Val Lys Ala Arg Ala Glu Ala Leu Gln Ala Ala Met
145                 150                 155                 160 atc tct gtc gat ctc cct ggt ggc gag gaa ttt ctg ctc tcg cct gcc       528
Ile Ser Val Asp Leu Pro Gly Gly Glu Glu Phe Leu Leu Ser Pro Ala
                165                 170                 175 ggg cag aat cca ttg ctg aag aag atg gtc gaa gag ttt gtg ccg cga       576
Gly Gln Asn Pro Leu Leu Lys Lys Met Val Glu Glu Phe Val Pro Arg
            180                 185                 190 ttt gca cct cgc tcg acg gtg ctc tac ctc ggg gat act cgt gga aag       624
Phe Ala Pro Arg Ser Thr Val Leu Tyr Leu Gly Asp Thr Arg Gly Lys
            195                 200                 205 cat tcc cta ttc gaa cga gag atc ttt gaa gag gtg ctc ggc ctg act       672
His Ser Leu Phe Glu Arg Glu Ile Phe Glu Glu Val Leu Gly Leu Thr
    210                 215                 220 ttc gac ccc cat ggt cga atg ccg gac ctt att ctc cat gac gaa gtt       720
Phe Asp Pro His Gly Arg Met Pro Asp Leu Ile Leu His Asp Glu Val
225                 230                 235                 240 cgt ggg tgg ctt ttc ctt atg gag gcc gtg aaa agt aaa ggt ccg ttt       768
Arg Gly Trp Leu Phe Leu Met Glu Ala Val Lys Ser Lys Gly Pro Phe
                245                 250                 255 gat gag gag cgg cat cgc agc ctg caa gag cta ttc gtt aca cct tca       816
Asp Glu Glu Arg His Arg Ser Leu Gln Glu Leu Phe Val Thr Pro Ser
            260                 265                 270 gcg ggt cta att ttt gta aac tgc ttt gaa aat cgt gag tcg atg cgt       864
Ala Gly Leu Ile Phe Val Asn Cys Phe Glu Asn Arg Glu Ser Met Arg
            275                 280                 285 cag tgg ctc cct gag ctg gct tgg gaa act gag gcg tgg gta gcg gaa       912
Gln Trp Leu Pro Glu Leu Ala Trp Glu Thr Glu Ala Trp Val Ala Glu
    290                 295                 300 gat cca gac cat ctg att cac ctt aac ggg tct aga ttt ctt ggg ccg       960
Asp Pro Asp His Leu Ile His Leu Asn Gly Ser Arg Phe Leu Gly Pro
305                 310                 315                 320 tac gaa cgt tag                                                       972
Tyr Glu Arg <210> SEQ ID NO 4
<211> LENGTH: 323
<212> TYPE: PRT
<213> ORGANISM: streptomyces species Bf-61

<400> SEQUENCE: 4

Met Asn Ser Ser Asp Gly Ile Asp Gly Thr Val Ala Ser Ile Asp Thr
1               5                   10                  15

Ala Arg Ala Leu Leu Lys Arg Phe Gly Phe Asp Ala Gln Arg Tyr Asn
            20                  25                  30

Val Arg Ser Ala Val Thr Leu Leu Ala Leu Ala Gly Leu Lys Pro Gly
        35                  40                  45

Asp Arg Trp Val Asp Ser Thr Thr Pro Arg Leu Gly Val Gln Lys Ile
```

```
            50                  55                  60
Met Asp Trp Ser Gly Glu His Trp Ala Lys Pro Tyr Ala Thr Gly Ser
 65                  70                  75                  80

Arg Glu Asp Phe Arg Lys Lys Thr Leu Arg Gln Trp Val Asp Asn Gly
                 85                  90                  95

Phe Ala Val Leu Asn Ala Asp Asn Leu Asn Ile Ala Thr Asn Ser Gln
            100                 105                 110

Leu Asn Glu Tyr Cys Leu Ser Asp Glu Ala Leu Gln Ala Leu Arg Ala
            115                 120                 125

Tyr Gly Thr Glu Gly Phe Glu Glu Ser Leu Val Val Phe Leu Asp Glu
130                 135                 140

Ala Ser Lys Ala Val Lys Ala Arg Ala Glu Ala Leu Gln Ala Ala Met
145                 150                 155                 160

Ile Ser Val Asp Leu Pro Gly Gly Glu Glu Phe Leu Leu Ser Pro Ala
                165                 170                 175

Gly Gln Asn Pro Leu Leu Lys Lys Met Val Glu Glu Phe Val Pro Arg
            180                 185                 190

Phe Ala Pro Arg Ser Thr Val Leu Tyr Leu Gly Asp Thr Arg Gly Lys
            195                 200                 205

His Ser Leu Phe Glu Arg Glu Ile Phe Glu Glu Val Leu Gly Leu Thr
210                 215                 220

Phe Asp Pro His Gly Arg Met Pro Asp Leu Ile Leu His Asp Glu Val
225                 230                 235                 240

Arg Gly Trp Leu Phe Leu Met Glu Ala Val Lys Ser Lys Gly Pro Phe
                245                 250                 255

Asp Glu Glu Arg His Arg Ser Leu Gln Glu Leu Phe Val Thr Pro Ser
            260                 265                 270

Ala Gly Leu Ile Phe Val Asn Cys Phe Glu Asn Arg Glu Ser Met Arg
            275                 280                 285

Gln Trp Leu Pro Glu Leu Ala Trp Glu Thr Glu Ala Trp Val Ala Glu
290                 295                 300

Asp Pro Asp His Leu Ile His Leu Asn Gly Ser Arg Phe Leu Gly Pro
305                 310                 315                 320

Tyr Glu Arg

<210> SEQ ID NO 5
<211> LENGTH: 30
<212> TYPE: PRT
<213> ORGANISM: unknown
<220> FEATURE:
<223> OTHER INFORMATION: SbfI Endonuclease

<400> SEQUENCE: 5

Ser Asp Gly Ile Asp Gly Thr Val Ala Ser Ile Asp Thr Ala Arg Ala
 1               5                  10                  15

Leu Leu Lys Arg Phe Gly Phe Asp Ala Gln Arg Tyr Asn Val
                20                  25                  30

<210> SEQ ID NO 6
<211> LENGTH: 31
<212> TYPE: PRT
<213> ORGANISM: Unknown
<220> FEATURE:
<223> OTHER INFORMATION: SbfI Endonuclease

<400> SEQUENCE: 6

Val Glu Glu Phe Val Pro Arg Phe Ala Pro Arg Ser Thr Val Leu Tyr
```

```
            1               5                  10                 15
          Leu Gly Asp Thr Arg Gly Lys His Ser Leu Phe Glu Glu Glu Ile
                           20                 25                 30
```

<210> SEQ ID NO 7
<211> LENGTH: 21
<212> TYPE: DNA
<213> ORGANISM: unknown
<220> FEATURE:
<223> OTHER INFORMATION: primer

<400> SEQUENCE: 7
atgaactccg acggcatcga c                                       21

<210> SEQ ID NO 8
<211> LENGTH: 17
<212> TYPE: DNA
<213> ORGANISM: unknown
<220> FEATURE:
<223> OTHER INFORMATION: primer
<220> FEATURE:
<221> NAME/KEY: misc_feature
<222> LOCATION: (3)..(3)
<223> OTHER INFORMATION: n = G,A,C or T
<220> FEATURE:
<221> NAME/KEY: misc_feature
<222> LOCATION: (6)..(6)
<223> OTHER INFORMATION: y = c or t
<220> FEATURE:
<221> NAME/KEY: misc_feature
<222> LOCATION: (9)..(9)
<223> OTHER INFORMATION: r = a or g
<220> FEATURE:
<221> NAME/KEY: misc_feature
<222> LOCATION: (12)..(12)
<223> OTHER INFORMATION: n = g,a,c or t

<400> SEQUENCE: 8
aanacyaart cnaccat                                            17

<210> SEQ ID NO 9
<211> LENGTH: 21
<212> TYPE: DNA
<213> ORGANISM: unknown
<220> FEATURE:
<223> OTHER INFORMATION: primer

<400> SEQUENCE: 9
atgaacagcg acggcatcga c                                       21

<210> SEQ ID NO 10
<211> LENGTH: 20
<212> TYPE: DNA
<213> ORGANISM: unknown
<220> FEATURE:
<223> OTHER INFORMATION: primer
<220> FEATURE:
<221> NAME/KEY: misc_feature
<222> LOCATION: (3)..(3)
<223> OTHER INFORMATION: s = g or c
<220> FEATURE:
<221> NAME/KEY: misc_feature
<222> LOCATION: (15)..(15)
<223> OTHER INFORMATION: s = g or c

<400> SEQUENCE: 10
aasaccaact cctcsaccat                                         20

<210> SEQ ID NO 11

```
<211> LENGTH: 27
<212> TYPE: DNA
<213> ORGANISM: unknown
<220> FEATURE:
<223> OTHER INFORMATION: primer

<400> SEQUENCE: 11
ggagccatac agagagcgat ttattcg                                           27

<210> SEQ ID NO 12
<211> LENGTH: 27
<212> TYPE: DNA
<213> ORGANISM: unknown
<220> FEATURE:
<223> OTHER INFORMATION: primer

<400> SEQUENCE: 12
ttgaaatcga attaataagt ctggatg                                           27

<210> SEQ ID NO 13
<211> LENGTH: 24
<212> TYPE: DNA
<213> ORGANISM: unknown
<220> FEATURE:
<223> OTHER INFORMATION: primer

<400> SEQUENCE: 13
ccagtccatg atcttctgaa cgcc                                              24

<210> SEQ ID NO 14
<211> LENGTH: 24
<212> TYPE: DNA
<213> ORGANISM: unknown
<220> FEATURE:
<223> OTHER INFORMATION: primer

<400> SEQUENCE: 14
cttcggcagt gggttgataa tggc                                              24

<210> SEQ ID NO 15
<211> LENGTH: 24
<212> TYPE: DNA
<213> ORGANISM: unknown
<220> FEATURE:
<223> OTHER INFORMATION: primer

<400> SEQUENCE: 15
agggagatcg acagagatca tcgc                                              24

<210> SEQ ID NO 16
<211> LENGTH: 24
<212> TYPE: DNA
<213> ORGANISM: unknown
<220> FEATURE:
<223> OTHER INFORMATION: primer

<400> SEQUENCE: 16
tactgcgcgg gcgctgctaa agcg                                              24

<210> SEQ ID NO 17
<211> LENGTH: 18
<212> TYPE: DNA
<213> ORGANISM: unknown
<220> FEATURE:
<223> OTHER INFORMATION: primer

<400> SEQUENCE: 17
```

```
gcggcaacct tcatccgg                                          18

<210> SEQ ID NO 18
<211> LENGTH: 24
<212> TYPE: DNA
<213> ORGANISM: unknown
<220> FEATURE:
<223> OTHER INFORMATION: primer

<400> SEQUENCE: 18
agggagatcg acagagatca tcgc                                   24

<210> SEQ ID NO 19
<211> LENGTH: 24
<212> TYPE: DNA
<213> ORGANISM: unknown
<220> FEATURE:
<223> OTHER INFORMATION: primer

<400> SEQUENCE: 19
tactgcgcgg gcgctgctaa agcg                                   24

<210> SEQ ID NO 20
<211> LENGTH: 24
<212> TYPE: DNA
<213> ORGANISM: unknown
<220> FEATURE:
<223> OTHER INFORMATION: primer

<400> SEQUENCE: 20
agcggataac aatttcacac agga                                   24

<210> SEQ ID NO 21
<211> LENGTH: 24
<212> TYPE: DNA
<213> ORGANISM: unknown
<220> FEATURE:
<223> OTHER INFORMATION: primer

<400> SEQUENCE: 21
cgccagggtt ttcccagtca cgac                                   24

<210> SEQ ID NO 22
<211> LENGTH: 24
<212> TYPE: DNA
<213> ORGANISM: unknown
<220> FEATURE:
<223> OTHER INFORMATION: primer

<400> SEQUENCE: 22
ccagtccatg atcttctgaa cgcc                                   24

<210> SEQ ID NO 23
<211> LENGTH: 36
<212> TYPE: DNA
<213> ORGANISM: unknown
<220> FEATURE:
<223> OTHER INFORMATION: primer

<400> SEQUENCE: 23
tggggcgaat tcccagtcca tgatcttctg aacgcc                      36

<210> SEQ ID NO 24
<211> LENGTH: 25
<212> TYPE: DNA
```

```
<213> ORGANISM: unknown
<220> FEATURE:
<223> OTHER INFORMATION: primer

<400> SEQUENCE: 24
tggggcaagc ttgatcaggt ccgtg                                  25

<210> SEQ ID NO 25
<211> LENGTH: 28
<212> TYPE: DNA
<213> ORGANISM: unknown
<220> FEATURE:
<223> OTHER INFORMATION: primer

<400> SEQUENCE: 25
tggggcaagc ttcgcctgct ggttgacc                               28

<210> SEQ ID NO 26
<211> LENGTH: 28
<212> TYPE: DNA
<213> ORGANISM: unknown
<220> FEATURE:
<223> OTHER INFORMATION: primer

<400> SEQUENCE: 26
tgtggggcaa gcttcgcccc ggtcgtcc                               28

<210> SEQ ID NO 27
<211> LENGTH: 27
<212> TYPE: DNA
<213> ORGANISM: unknown
<220> FEATURE:
<223> OTHER INFORMATION: primer

<400> SEQUENCE: 27
tggggcaagc ttctgcgatc cgctgcc                                27

<210> SEQ ID NO 28
<211> LENGTH: 30
<212> TYPE: DNA
<213> ORGANISM: unknown
<220> FEATURE:
<223> OTHER INFORMATION: primer

<400> SEQUENCE: 28
tggggcaagc ttcgttggcg gtgctcccgc                             30

<210> SEQ ID NO 29
<211> LENGTH: 24
<212> TYPE: DNA
<213> ORGANISM: unknown
<220> FEATURE:
<223> OTHER INFORMATION: primer

<400> SEQUENCE: 29
gagcaatgtc acagcgctac ggac                                   24

<210> SEQ ID NO 30
<211> LENGTH: 24
<212> TYPE: DNA
<213> ORGANISM: unknown
<220> FEATURE:
<223> OTHER INFORMATION: primer

<400> SEQUENCE: 30
gatccaacac agtcgagttc aacc                                   24
```

```
<210> SEQ ID NO 31
<211> LENGTH: 24
<212> TYPE: DNA
<213> ORGANISM: unknown
<220> FEATURE:
<223> OTHER INFORMATION: primer

<400> SEQUENCE: 31
aacggcaaac ggcgaaagag gacc                                          24

<210> SEQ ID NO 32
<211> LENGTH: 24
<212> TYPE: DNA
<213> ORGANISM: unknown
<220> FEATURE:
<223> OTHER INFORMATION: primer

<400> SEQUENCE: 32
cctcatgctt tggttgaact cgac                                          24

<210> SEQ ID NO 33
<211> LENGTH: 24
<212> TYPE: DNA
<213> ORGANISM: unknown
<220> FEATURE:
<223> OTHER INFORMATION: primer

<400> SEQUENCE: 33
tcgttgcttt cagtgtgagg ccgc                                          24

<210> SEQ ID NO 34
<211> LENGTH: 24
<212> TYPE: DNA
<213> ORGANISM: unknown
<220> FEATURE:
<223> OTHER INFORMATION: primer

<400> SEQUENCE: 34
cgttgtgccc atggtttatc agtc                                          24

<210> SEQ ID NO 35
<211> LENGTH: 24
<212> TYPE: DNA
<213> ORGANISM: unknown
<220> FEATURE:
<223> OTHER INFORMATION: primer

<400> SEQUENCE: 35
ctcttgcttt accttcgtgt ccgc                                          24

<210> SEQ ID NO 36
<211> LENGTH: 30
<212> TYPE: PRT
<213> ORGANISM: unknown
<220> FEATURE:
<223> OTHER INFORMATION: R.SbfI

<400> SEQUENCE: 36

Ser Asp Gly Ile Asp Gly Thr Val Ala Ser Ile Asp Thr Ala Arg Ala
1               5                   10                  15

Leu Leu Lys Arg Phe Gly Phe Asp Ala Gln Arg Tyr Asn Val
            20                  25                  30

<210> SEQ ID NO 37
```

```
<211> LENGTH: 33
<212> TYPE: PRT
<213> ORGANISM: unknown
<220> FEATURE:
<223> OTHER INFORMATION: R.SbfI

<400> SEQUENCE: 37

Met Asn Ser Ser Asp Gly Ile Asp Gly Thr Val Ala Ser Ile Asp Thr
1               5                   10                  15

Ala Arg Ala Leu Leu Lys Arg Phe Gly Phe Asp Ala Gln Arg Tyr Asn
            20                  25                  30

Val

<210> SEQ ID NO 38
<211> LENGTH: 24
<212> TYPE: DNA
<213> ORGANISM: unknown
<220> FEATURE:
<223> OTHER INFORMATION: primer

<400> SEQUENCE: 38
ggccacgtaa acgttcggta catc                                          24

<210> SEQ ID NO 39
<211> LENGTH: 24
<212> TYPE: DNA
<213> ORGANISM: unknown
<220> FEATURE:
<223> OTHER INFORMATION: primer

<400> SEQUENCE: 39
tcatttcgct caaagagcag gggc                                          24

<210> SEQ ID NO 40
<211> LENGTH: 27
<212> TYPE: DNA
<213> ORGANISM: unknown
<220> FEATURE:
<223> OTHER INFORMATION: primer

<400> SEQUENCE: 40
ggagccatac agagagcgat ttattcg                                       27

<210> SEQ ID NO 41
<211> LENGTH: 27
<212> TYPE: DNA
<213> ORGANISM: unknown
<220> FEATURE:
<223> OTHER INFORMATION: primer

<400> SEQUENCE: 41
ttgaaatcga attaataagt ctggatg                                       27

<210> SEQ ID NO 42
<211> LENGTH: 57
<212> TYPE: DNA
<213> ORGANISM: unknown
<220> FEATURE:
<223> OTHER INFORMATION: primer

<400> SEQUENCE: 42
ttccgggatc cggaggttta aaatatgact aagcggcaac acaattacct atatctc      57

<210> SEQ ID NO 43
<211> LENGTH: 48
```

<212> TYPE: DNA
<213> ORGANISM: unknown
<220> FEATURE:
<223> OTHER INFORMATION: primer

<400> SEQUENCE: 43
ttgccgcatg cgtcgttaca ttagctgcaa actctgattg attatttc          48

<210> SEQ ID NO 44
<211> LENGTH: 63
<212> TYPE: DNA
<213> ORGANISM: unknown
<220> FEATURE:
<223> OTHER INFORMATION: primer

<400> SEQUENCE: 44
tggctgcagg gatccggagg tttaaaatat gaacagcagt gacggcatcg acggaacggt    60
agc                                                                  63

<210> SEQ ID NO 45
<211> LENGTH: 51
<212> TYPE: DNA
<213> ORGANISM: unknown
<220> FEATURE:
<223> OTHER INFORMATION: primer

<400> SEQUENCE: 45
tcgggccccg ggctcgagtc taacgttcgt acggcccaag aaatctagac c             51

<210> SEQ ID NO 46
<211> LENGTH: 27
<212> TYPE: DNA
<213> ORGANISM: unknown
<220> FEATURE:
<223> OTHER INFORMATION: primer

<400> SEQUENCE: 46
ggagccatac agagagcgat ttattcg                                        27

<210> SEQ ID NO 47
<211> LENGTH: 27
<212> TYPE: DNA
<213> ORGANISM: unknown
<220> FEATURE:
<223> OTHER INFORMATION: primer

<400> SEQUENCE: 47
ttgaaatcga attaataagt ctggatg                                        27

<210> SEQ ID NO 48
<211> LENGTH: 24
<212> TYPE: DNA
<213> ORGANISM: unknown
<220> FEATURE:
<223> OTHER INFORMATION: primer

<400> SEQUENCE: 48
tactgcgcgg gcgctgctaa agcg                                           24

<210> SEQ ID NO 49
<211> LENGTH: 24
<212> TYPE: DNA
<213> ORGANISM: unknown
<220> FEATURE:
<223> OTHER INFORMATION: primer

```
<400> SEQUENCE: 49
aatttctgct ctcgcctgcc gggc                                      24

<210> SEQ ID NO 50
<211> LENGTH: 24
<212> TYPE: DNA
<213> ORGANISM: unknown
<220> FEATURE:
<223> OTHER INFORMATION: primer

<400> SEQUENCE: 50
ccagtccatg atcttctgaa cgcc                                      24

<210> SEQ ID NO 51
<211> LENGTH: 24
<212> TYPE: DNA
<213> ORGANISM: unknown
<220> FEATURE:
<223> OTHER INFORMATION: primer

<400> SEQUENCE: 51
agggagatcg acagagatca tcgc                                      24

<210> SEQ ID NO 52
<211> LENGTH: 58
<212> TYPE: DNA
<213> ORGANISM: unknown
<220> FEATURE:
<223> OTHER INFORMATION: primer

<400> SEQUENCE: 52
tggccgggat ccggaggttt aaaatatgca tccgatcgcc agcactgaaa ctcgccgc   58

<210> SEQ ID NO 53
<211> LENGTH: 47
<212> TYPE: DNA
<213> ORGANISM: unknown
<220> FEATURE:
<223> OTHER INFORMATION: primer

<400> SEQUENCE: 53
ttgccgcatg cctcacgagg cagattccgg aatctcacag aagagtc              47

<210> SEQ ID NO 54
<211> LENGTH: 27
<212> TYPE: DNA
<213> ORGANISM: unknown
<220> FEATURE:
<223> OTHER INFORMATION: primer

<400> SEQUENCE: 54
ggagccatac agagagcgat ttattcg                                   27

<210> SEQ ID NO 55
<211> LENGTH: 27
<212> TYPE: DNA
<213> ORGANISM: unknown
<220> FEATURE:
<223> OTHER INFORMATION: primer

<400> SEQUENCE: 55
ttgaaatcga attaataagt ctggatg                                   27

<210> SEQ ID NO 56
<211> LENGTH: 24
```

```
-continued

<212> TYPE: DNA
<213> ORGANISM: unknown
<220> FEATURE:
<223> OTHER INFORMATION: primer

<400> SEQUENCE: 56
ctttcccgta cttacaccga tgcc                                    24

<210> SEQ ID NO 57
<211> LENGTH: 24
<212> TYPE: DNA
<213> ORGANISM: unknown
<220> FEATURE:
<223> OTHER INFORMATION: primer

<400> SEQUENCE: 57
tcctcgatct tgggcgaacg ggcc                                    24
```

METHOD FOR CLONING AND EXPRESSION OF SBFI RESTRICTION ENDONUCLEASE AND SBFI METHYLASE IN *E. COLI*

BACKGROUND OF THE INVENTION

Present embodiments of the invention relate to recombinant DNA that encodes the SbfI restriction endonuclease (SbfI endonuclease; R.SbfI) as well as the SbfI modification methyltransferase (SbfI methyltransferase; M.SbfI), and to the expression of the SbfI endonuclease and methyltransferase in *E. coli* cells that contain the recombinant DNA.

Restriction endonucleases are enzymes that occur naturally in certain unicellular microbes—mainly bacteria and archaea—and that function to protect these organisms from infections by viruses and other parasitic DNA elements. Restriction endonucleases bind to specific sequences of nucleotides ('recognition sequence') in double-stranded DNA molecules (dsDNA) and cleave the DNA, usually within or close to the sequence, disrupting the DNA and triggering its destruction. Restriction endonucleases commonly occur with one or more companion enzymes termed modification methyltransferases. Methyltransferases bind to the same sequences in dsDNA as the restriction endonucleases they accompany, but instead of cleaving the DNA, they alter it by the addition of a methyl group to one of the bases within the sequence. This methylation ('modification') prevents the restriction endonuclease from binding to that site thereafter, rendering the site resistant to cleavage. Methyltransferases function as cellular antidotes to the restriction endonucleases they accompany, protecting the cell's own DNA from destruction by its restriction endonucleases. Together, a restriction endonuclease and its companion modification methyltransferase(s) form a restriction-modification (R-M) system, an enzymatic partnership that accomplishes for microbes what the immune system accomplishes, in some respects, for multicellular organisms.

A large and varied class of restriction endonucleases have been classified as 'Type II' restriction endonucleases. These enzymes cleave DNA at defined positions, and in purified form can be used to cut DNA molecules into precise fragments for gene cloning and analysis. The biochemical precision of Type II restriction endonucleases far exceeds anything achievable by chemical methods, making these enzymes the reagents sine qua non of molecular biology laboratories. In this capacity, as molecular tools for gene dissection, Type II restriction endonucleases have had a profound impact on the life sciences in the past 25 years, transforming the academic and commercial arenas, alike. Their utility has spurred a continuous search for new restriction endonucleases, and a large number have been found. Today more than 200 Type II endonucleases are known, each possessing different DNA cleavage characteristics (Roberts and Macelis, Nucl. Acids Res. 29:268–269 (2001)). (REBASE®, http://rebase.neb.com/rebase). Concomitantly, the production and purification of these enzymes has been improved by the cloning and over-expression of the genes that encode them in non-natural production strain host cells such as *E. coli*.

Since the various restriction enzymes appear to perform similar biological roles, in much the same ways, it might be thought that they would resemble one another closely in amino acid sequence and behavior. Experience shows this not to be true, however. Surprisingly, far from resembling one another, most Type II restriction enzymes appear unique, resembling neither other restriction enzymes nor any other known kind of protein. Type II restriction endonucleases seem to have arisen independently of one another for the most part during evolution, and to have done so hundreds of times, so that today's enzymes represent a heterogeneous collection rather than a discrete family. Some restriction endonucleases act as homodimers, some as monomers, others as heterodimers. Some bind symmetric sequences, others asymmetric sequences; some bind continuous sequences, others discontinuous sequences; some bind unique sequences, others multiple sequences. Some are accompanied by a single methyltransferase, others by two, and yet others by none at all. When two methyltransferases are present, sometimes they are separate proteins, at other times they are fused. The orders and orientations of restriction and modification genes vary, with all possible organizations occurring. Several kinds of methyltransferases exist, some methylating adenines (m6A-MTases), others methylating cytosines at the N-4 position (m4C-MTases), or at the 5 position (m5C-MTases). Usually there is no way of predicting, a priori, which modifications will block a particular restriction endonuclease, which kind(s) of methyltransferases(s) will accompany that restriction endonuclease in any specific instance, nor what their gene orders or orientations will be.

From the point of view of cloning a Type II restriction endonuclease, the great variability that exists among restriction-modification systems means that, for experimental purposes, each is unique. Each enzyme is unique in amino acid sequence and catalytic behavior; each occurs in unique enzymatic association, adapted to unique microbial circumstances; and each presents the experimenter with a unique challenge. Sometimes a restriction endonuclease can be cloned and over-expressed in a straightforward manner but more often than not it cannot, and what works well for one enzyme can work not at all for the next. Success with one is no guarantee of success with another.

SUMMARY OF THE INVENTION

In an embodiment of the invention, an isolated DNA encoding the SbfI restriction endonuclease is provided where the isolated DNA Is obtainable from *Streptomyces* species Bf-61.

In an additional embodiment of the invention, a recombinant DNA vector is provided that includes a vector into which a DNA segment encoding the SbfI restriction endonuclease has been inserted. A host cell transformed by the recombinant vector is further provided.

In an additional embodiment of the invention, an isolated DNA encoding the SbfI restriction endonuclease and SbfI methylase is provided where the isolated DNA Is obtainable from ATCC No. PTA-5371. A vector that includes this isolated DNA and a host cell transformed by the vector is further provided.

In an additional embodiment of the invention, a method is provided for producing recombinant SbfI restriction endonuclease that includes culturing a host cell transformed with any of the vectors described above under conditions suitable for expression of the endonuclease.

BRIEF DESCRIPTION OF THE DRAWINGS

FIG. 2. The SbfI methylase gene sequence (SbfIM, 1460 bp) (SEQ ID NO:1) and the encoded amino acid sequence (SEQ ID NO:2).

FIG. 3. The SbfI endonuclease gene sequence (SbfIR, 971 bp) (SEQ ID NO:3) and the encoded amino acid sequence (SEQ ID NO:4).

FIG. 4. A plasmid map of pACYC184-PstIM clone.

FIG. 5. A plasmid map of pACYC184-SbfIM clone.

FIG. 6. A plasmid map of pCAB16.

FIG. 7. A plasmid map of pLT7K-SbfIR endonuclease clone.

FIG. 8. Recombinant SbfI endonuclease activity in cell extract. l DNA was used as the substrate. Lanes 2–8, 1x, ½, ¼, ⅛, ⅟₁₆, ⅟₃₂, ⅟₆₄ diluted cell extract added in the restriction digestions. Lane 1, l DNA digested with native SbfI.

DETAILED DESCRIPTION OF THE INVENTION

Figure 1:
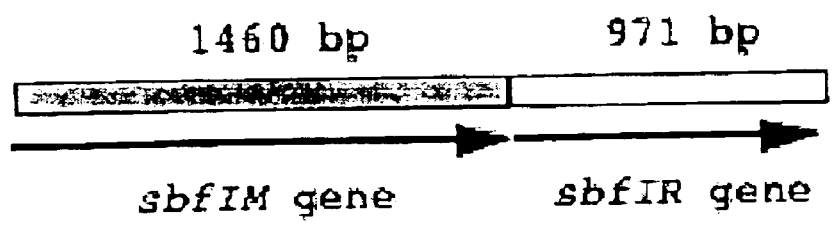
FIG. 1. Gene organization of the SbfI R-M system. SbfIR, SbfI restriction endonuclease gene; SbfIM, SbfI methylase gene.

The SbfI endonuclease and methyltransferase are enzymes that occur in the bacterium *Streptomyces* species Bf-61 (New England Biolabs' strain collection). The SbfI endonuclease binds to the symmetric nucleotide (nt) sequence 5'-CCTGCAGG-3' in double-stranded DNA molecules (dsDNA) and cleaves the DNA between the A and G in each strand thus: 5'-CCTGCA/GG-3', producing DNA fragments with 4-nt cohesive ends (/ indicates the position of strand-cleavage). Many restriction endonucleases that occur in nature are accompanied by protective modification methyltransferases. However, restriction endonucleases that recognize and cleave long, infrequently occurring sequences such as R.SbfI, are not always accompanied by a protective methyltransferase. At the outset of these experiments it was not known whether a modification methyltransferase in fact accompanied R.SbfI.

Hurdles in Cloning SbfI Restriction Endonuclease (a) Unsuccessful Methylase Selection The methylase selection method described in U.S. Pat. No. 5,200,333 is the preferred method for cloning restriction-modification systems. Methylase selection did not however yield the SbfI methylase gene (M.SbfI). The reasons for failure could include any or all of the following technical difficulties:

construction of initial libraries where potential cloning sites may cut within the methylase gene; failure to clone the proper fragment from the libraries due to size of the DNA fragment;

gene toxicity; low expression of the methylase gene, or the complete absence of the accompanying methylase gene, as with certain other 8-nucleotide specific restriction endonucleases such as PacI 5-TTAAT/TAA-3' (U.S. Pat. No. 5,098,839).

(b) Absence of SbfIM Downstream Of SbfIR

Although the possibility existed that there was no M.SbfI, alternative approaches to cloning the gene were attempted. Subsequently an SbfI methyltransferase was indeed identified by a PCR reaction on the original pUC19-Sau3AI partial SbfI DNA library that failed to yield a selectable sbfIM gene. The PCR reaction showed the presence of a Sau3AI partial fragment that contained the sbfIM region. The location of the sbfIM region on chromosomal DNA was eventually determined by inverse PCR to be not downstream of the sbfIR gene as first thought but upstream of the sbfIR gene. The sequence of sbfIM was subsequently obtained.

The SbfI methylase gene was cloned by PCR from S. Bf-61 chromosomal DNA into pACYC184 and transformed into *E. coli*. The cloned SbfI methyltransferase bound to the same nucleotide (nt) sequence in dsDNA as R.SbfI, and catalyzed the addition of a methyl group to the adenine residue in each strand (5'-CCTGCmAGG-3'), producing modified DNA molecules that was resistant to cleavage by R.SbfI (mA indicates the modified base).

The SbfI restriction endonuclease gene (sbfIR) was identified using PCR primers based on the SbfI endonuclease (R.SbfI) amino acid sequence from the N-terminal end and the cyanogen bromide-digested ends of the protein. The gene was subsequently cloned by inverse PCR from SbfI chromosomal DNA.

(c) Inconclusive Expression Levels for Endonuclease

The PCR fragment obtained by inverse PCR containing the sbfIR gene was inserted into the plasmid vectors pRRS and pLT7K and used to transform M.PstI pre-modified *E. coli*. M.PstI premodification was used because M.SbfI had not yet been identified and PstI methylase (M.PstI) was shown to protect SbfI sites in addition to PstI sites against both PstI and SbfI endonuclease digestion of purified PstI methylated DNA.

No clones with inserts were found with pRRS; some clones were found with pLT7K where the regulated T7 expression vector pLT7K contained a constitutive anti-sense promoter downstream of sbfIR to reduce basal expression. Some pLT7K clones contained correct DNA sequence, however these produced very low SbfI endonuclease activity upon induction. This negative result suggested there was selection pressure to isolate endonuclease mutants with reduced activity. This disappointing result suggested that highly expressing clones were being selected against perhaps because of under-methylation of the host chromosome DNA by M.PstI.

Since expression from a medium-copy-number T7 vector in *E. coli* pre-modified with M.PstI did not generate a stable high expression clone, efforts were made to express the sbfIR gene in M.SbfI methylated *E. coli* using pLT7K. When the SbfI endonuclease gene was cloned in M.SbfI pre-modified *E. coli*, a stable and over-expressing clone was established. Over-expression of an enzyme is generally intended to mean at least $10^5$ units/g including $10^6$ or $10^7$ units/g. Low expression is less than $10^3$ ug. Low expression levels of a putative cloned restriction endonuclease may result in cleavage profiles of DNA. However, this does not conclusively prove that the desired enzyme has been obtained. For example, the enzyme digest may be partial or incomplete making it unclear whether the products are merely the result of random cleavage.

(d) Obtaining an Over-Expressing Clone

A stable over-expressing clone of R.SbfI was obtained as follows: The sbfIR gene was amplified by PCR from genomic DNA. Following purification, the resulting PCR fragment was blunt-end ligated into pCAB16 at a BsaAI site. pCAB16 is a pUC18 derivative containing the mspIR gene in the polylinker of pUC18 in line with the Plac promoter. pCAB16 contains a single BsaAI site within the mspIR gene. Insertions at this site interrupt mspIR expression (which would otherwise be lethal) enabling plasmids containing inserts to be selectively recovered with high efficiency (FIG. 6). The sbfIR PCR-fragment was ligated into the BsaAI site of pCAB16, and transformed into M.PstI pre-modified *E. coli*. Clones that were found to carry the sbfIR PCR insert were cultured. However, assays showed these clones had no detectable SbfI endonuclease activity. DNA sequencing of these clones showed that an intact sbfIR gene was present in the opposite orientation to Plac and mspIR, which could explain the lack of R.SbfI activity.

Taking an alternative approach, the sbfIR gene was purified from the pCAB16-SbfIR plasmid by gel purification. The resulting DNA fragment was ligated into pLT7K and transformed into M.PstI pre-modified *E. coli*. Clones found to carry the PCR insert were induced with IPTG and assayed for SbfI activity on λ DNA. The extracts generated partial SbfI digestion pattern. DNA sequence of one of these clones showed that it carried an intact sbfIR gene. Since the DNA sequence was correct for this pLT7K-sbfIR plasmid, most likely highly expressing clones were being selected against during induction. When the sbfIM gene was subsequently identified and cloned into pACYC184, this same pLT7K-SbfIR clone was then transformed into M.SbfI pre-modified *E. coli*. Transformants in which the sbfIM gene was expressed from a low-copy-number plasmid pACYC184 and the sbfIR gene was expressed using the medium-copy-number pLT7K within the same *E. coli* host were cultured and their cells extracts were assayed for SbfI activity on λ DNA. The recombinant SbfI endonuclease yield was ~$10^5$ units/g of wet cells from the over-producing strain.

In summary, an expression strategy was ultimately developed which overcame a number of hurdles and ultimately proved successful in yielding over-expressed R.SbfI. This strategy relied in one embodiment on expressing the R.SbfI and M.SbfI under different strength promoters namely a medium copy number promoter and a low copy number promoter respectively. However, in alternative embodiments, both sbfIM and sbfIR genes may be expressed under the same promoter.

Moreover, the sbfIM gene may be cloned in a single plasmid together with the sbfIR gene under the same or different promoters or in seperate plasmids under the same or different promoters.

The method described herein by which the sbfIM and sbfIR genes are preferably cloned and expressed in *E. coli* include the following steps:

Preparation of Genomic DNA and Construction of SbfI Genomic DNA Library

Genomic DNA was prepared from *Streptomyces* species Bf-61 by the 2×Kirby method ((Hopwood et al. *Genetic Manipultation of Streptomyces*. A Laboratory Manual. John Innes Foundation, Norwich. p. 77 (1985)).

Partially digested genomic DNA preparations were ligated to a digested, CIP-treated pUC19 vector into which two SbfI sites had been previously engineered. The ligated DNA mixtures were used to transform *E. coli*. Transformants from each library were pooled and amplified, and plasmid DNA was prepared to generate primary plasmid libraries.

Methylase-selection

The primary plasmid libraries were challenged by digestion with SbfI. These DNA digests were then transformed back into *E. coli* and plasmid DNA was prepared from some of these initial the survivors of each selected primary library. SbfI digestion of these indicated that none were resistant to digestion, suggesting that none carried the sbfIM gene. Remaining surviving colonies from some of the challenged primary libraries were also pooled to form a secondary library, and challenged a second time with SbfI. Plasmid DNA of these survivors again showed no resistance to SbfI endonuclease digestion.

The non-recombinant SbfI endonuclease was purified and the N-terminal amino acid sequence of this protein was determined along with the amino acid sequence from cyanobromide digested R.SbfI fragments. Based on these amino acid sequences, converging sets of degenerate and non-degenerate primers were synthesized. These were used to prime PCR reactions on SbfI chromosomal DNA generating DNA fragments containing the 5' end of the sbfIR gene. DNA sequencing revealed an open reading frame (ORF) of 555 bp that had extensive homology to the R.PstI endonuclease and to its isoschizomers, BsuBI and XphI. The PstI recognition sequence, 5'-CTGCA/G-3', is encompassed by the SbfI recognition sequence, 5'-CCTGCA/GG-3'. These similarities in recognition sequences and amino acid sequences strongly suggested that the 555 bp ORF comprised the 5' end of sbfIR gene.

Inverse PCR Amplification of DNA Downstream of the 5' End SbfI Endonuclease Gene Following cloning and identification of the N-terminal portion of the sbfIR endonuclease gene, efforts were made to clone 3' end of sbfIR and the adjacent downstream DNA.

Genomic DNA was digested with multiple restriction enzymes and self-ligated. The resulting circular DNA molecules were used as templates for inverse PCR. The DNA sequence at the N-terminus of the sbfIR gene was used to design primers for the inverse PCR of SbfI chromosomal DNA.

Not all inverse PCR reactions of self-ligated genomic DNA generated inverse PCR fragments. Only the HincII and HpyCH4HIV templates produced PCR fragments that could be purified for cloning. The HincII- and HpyCH4HIV-inverse PCR fragments were ligated into pUC19 and transformed into *E. coli*. Clones with PCR inserts were sequenced directly with pUC19 universal primers.

From this DNA sequence near the newly found HincII site, a new primer was designed and was used in a PCR reaction with a primer from the N-terminal SbfI endonuclease sequence to generate a fragment that linked the N-terminal sequence to the inverse PCR sequence downstream of 5' sbfIR. The PCR fragment was purified, digested and ligated into pUC19. This ligated DNA was transformed into *E. coli* and clones with PCR inserts were sequenced directly with pUC19 universal primers.

The HincII and HpyCH4HIV PCR overlapping fragments generated ~900 bp, and ~500 bp of new sequences, respectively. Combining these sequences with the 5' sbfIR sequence, a complete ORF of 969 bp was found, most likely representing the sbfIR restriction gene. An additional ~700 bp of sequenced SbfI chromosomal DNA that was downstream of sbfIR was compared to the known gene products in GenBank using BLAST and did not appear to contain the SbfI methylase gene.

Inverse PCR Amplification of DNA Upstream of SbfI Endonuclease and Identification of SbfI Methylase Unable to isolate the sbfIM gene by methylase selection, combined with the inability to identify the sbfIM gene downstream of the SbfI endonuclease, efforts were made to clone DNA upstream of the sbfIR gene.

PCR reactions were done on the SbfI primary pUC19 libraries used in the initial methylase selection with two converging primers within the sbfIR gene. PCR showed that the SbfI primary libraries contained at least a portion of the sbfIR gene. To identify any larger upstream DNA fragments that might be contained in the initial primary libraries, a second PCR was done on the libraries with pUC19 universal primers and a primer designed from within the sbfIR gene oriented toward the upstream or 5' end of sbfIR. These atypical PCR reactions generated fragments from the Bg/II, Bc/I and Sau3 AI primary libraries that were larger than 1.6 kb and potentially large enough to contain upstream DNA for the sbfIM gene. These library generated PCR fragments were purified and DNA sequenced directly using the PCR primers.

The only readable sequence came from the SbfI Sau3AI library PCR fragment. This DNA sequence was used to design a set of new PCR primers to be used in PCR with a converging primer from within the sbfIR gene to hopefully directly clone the DNA upstream relative to the sbfIR gene from SbfI chromosomal DNA. These PCR fragments were purified, digested, and ligated into pUC19 with compatible ends, followed by transformation in E. coli. Colony PCR identified PCR inserts and clones containing about the correct size fragment were further purified by CsCl purification and sequenced with pUC19 universal and custom primers.

DNA sequencing revealed a new upstream ORF, which was determined to be the 3' end of the sbfIM gene, which was coupled and arranged in head-to-tail fashion to the sbfIR gene. The sbfIM transcriptional (TGA) stop codon was found to overlap the GTG start codon for the SbfI endonuclease gene. DNA sequencing across the junction revealed that along with the GTG start for the sbfIR gene, an additional translated amino acid, serine (S), is present making R.SbfI one amino acid longer than predicted from N-terminal amino acid sequence. In fact R.SbfI is actually 323 amino acids in length, not 322 amino acids. With the additional serine, the full sbfIR gene is 971 bp. (FIG. 3).

Unpredictably during cloning, due to a designed HindIII site In the PCR primer, DNA sequencing revealed an unknown HindIII site contained within the sbfIM gene. This truncated the PCR fragment during cloning and in effect cut off the 5' end of the sbfIM gene. Efforts were then made to clone 5' end of sbfIM using inverse PCR with new primers designed from within the truncated sbfIM gene. Inverse PCR was performed on genomic DNA digested with HincII and self-ligated. The resulting PCR fragments were purified, ligated into pCAB16 and transformed into E. coli. Plasmid DNAs were purified and sequenced. Combining this DNA sequence with the truncated 3' sbfIM gene DNA sequence, the full length sbfIM gene of 1460 bp was revealed, which encodes a translated SbfI methylase of 496 amino acids (FIG. 2).

Isolation of Intact SbfIR Gene in E. Coli

Since the sbfIM gene was not isolated initially, the cloning/expression strategy was to use M.PstI to pre-modify E. coli by expressing the pstIM gene in a low copy-number plasmid, pACYC184, and the sbfIR gene in either a high copy-number constitutive vector pRRS, or a medium-copy-number, regulated vector, pLT7K.

The sbfIR gene was amplified from genomic DNA by PCR with Deep Vent® DNA polymerase. Following purification and digestion the PCR fragment was ligated into pRRS and pLT7K, respectively, digested with the same enzymes to create compatible ends. The pRRS-SbfIR ligation was transformed into M.PstI pre-modified E. coli and plasmids were purified and screened for inserts. No pRRS-SbfIR clones were found. The pLT7K-SbfIR ligation was transformed into E. coli ER2502 (lacking T7 RNA polymerase). Positive clones were identified and these were then transferred into a M.PstI E. coli ER2744 (containing the T7 RNA polymerase). Cell cultures were made from individual pLT7K-SbfIR transformants and induced with IPTG. Cell extracts were prepared and assayed for SbfI endonuclease activity and none produced detectable SbfI endonuclease.

In another attempt, a larger PCR fragment containing the sbfIR gene plus 600 bp of downstream DNA (~1500 bp), was digested and ligated into pLT7K and transformed into E. coli. Positive clones were identified and then transferred into M.PstI pre-modified E. coli ER2744 and induced with IPTG, assayed for SbfI activity, yielding no detectable activity. This same pLT7K-SbfIR ligation of the sbfIR gene, including 600 bp of downstream DNA, was also directly transformed into M.PstI pre-modified E. coli ER2744. Positive pLT7K-SbfIR clones were identified by PCR, cultured, induced with IPTG and then assayed again yielding no detectable SbfI activity. This negative result indicated there was selection pressure to isolate endonuclease mutants.

In order to isolate a clone containing the sbfIR gene with the correct DNA sequence from the native Streptomyces species Bf-61 strain, the sbfIR gene PCR was blunt-end ligated into pCAB16 at the BsaAI site followed by tranformation into M.PstI pre-modified E. coli. Clones were found to carry the sbfIR gene fragment, and cultured, and assayed for SbfI activity on λ DNA. The extracts generated no SbfI digestion pattern, however, DNA sequence from these clones showed an intact sbfIR gene in the opposite orientation to Plac and mspIR.

Expression of SbfIR Gene in E. coli

The sbfIR gene was gel purified from the pCAB16-SbfIR plasmid, ligated into pLT7K and transformed into M.PstI pre-modified E. coli. Clones were found to carry the sbfIR gene and assayed for SbfI activity on λ DNA. The extracts generated partial SbfI digestion pattern. DNA sequencing of pLT7K-SbfIR clones showed that each carried an intact sbfIR gene. Since the DNA sequence was correct for the pLT7K-SbfIR #12 plasmid, when the sbfIM gene was identified and cloned into pACYC184, the pLT7K-SbfIR #12 clone was then transformed into M.SbfI pre-modified E. coli. All transformants were cultured, induced with IPTG and then assayed for SbfI activity on λ DNA yielding ~$10^5$ units/g of wet cells from the over-producing strain.

The present invention is further illustrated by the following Examples. These Examples are provided to aid in the understanding of the invention and are not construed as a limitation thereof.

All references cited above and below are herein incorporated by reference.

EXAMPLE 1

Cloning of SbfI Restriction-Modification System in E. coli

1. Preparation of genomic DNA Genomic DNA was prepared from 2 g of Streptomyces species Bf-61, by the following steps:

a. Cell wall digestion by addition of lysozyme (2 mg/ml final), sucrose (1% final), and 50 mM Tris-HCl, pH 8.0.

b. Cell lysis by addition of 8 ml of 2×Kirby mixture: (2 g Sodium tri-isopropylnaphthalene sulphonate, 12 g 4-amino-salicylate, 10 ml 1M Tris-HCl pH8, 6 ml phenol saturated with 50 mM Tris-HCl pH 8.0 made up in 100 ml $dH_2O$) Vortex 1 minute.

C. Removal of proteins by phenol-$CHCl_3$ extraction of DNA 2 times (equal volume).

d. Dialysis in 4 liters of TE buffer, buffer change four times.

e. RNase A treatment to remove RNA.

f. Genomic DNA precipitation in 0.4M NaCl and 0.55 volume of 100% isopropanol, spooled, dried and resuspended in TE buffer.

2. Restriction digestion of genomic DNA and construction of genomic DNA library

Varying units of restriction enzymes Sau3AI, BC/I, BstYI, Bg/II, XbaI and NheI were used to digest 10 μg genomic DNA to achieve complete and limited partial digestion. The digested DNA was purified via phenol-$CHCl_3$ extraction and isopropanol precipitation. The Sau3AI-, Bc/I-, BstYI-, and Bg/II-, digested DNAs were ligated to BamHI- digested and CIP-treated pUC19 vector containing 2 SbfI sites. XbaI- and NheI-, digested DNAs were ligated to the same vector XbaI- digested and CIP treated. Following overnight ligation, the DNA was used to transform an endA⁻ host (ER2502, ER2683 New England Biolabs' collection (Beverly, Mass.)), made competent by $CaCl_2$ method. Approximately 2–5,000 $Ap^R$ transformants were obtained from each library. For each enzyme, colonies were pooled and amplified in 500 ml LB+Amp overnight. Plasmid DNA was prepared by CsCl gradient purification, resulting in a primary library.

3. Attempt to Clone SbfIM gene by methylase selection

The primary plasmid DNA library (1 μg DNA) was challenged by digestion with ~30 units of SbfI at 37° C. for 1 hour. The digested DNA was transferred Into ER2502 or ER2683 by transformation, resulting in ~750 $Ap^R$ survivors from all libraries. Plasmid DNA from ~120 survivors was prepared by the Compass Mini Plasmid Kit method, followed by SbfI digestion. No resistant clones were found from any of the libraries. Some remaining survivors (Sau3AI, BstYI, XbaI and NheI) were also pooled separately to form secondary libraries, challenged with SbfI a second time, followed by the same survivor Plasmid DNA purification, again no resistant clones were found.

4. Identification of the SbfI endonuclease

The non-recombinant SbfI endonuclease was purified to near homogeneity and the purified protein was subjected to SDS-PAGE. A protein band of ~36 kDa was detected. The N-terminal amino acid sequence was determined as (MN)SDGIDGTV ASIDTARALLKRFGFDAQRYNV (SEQ ID NO:5). The 36 kDa protein was digested with cyanogen bromide and a 4.5 kDa fragment amino acid sequence was determined as (M)VEEFVPRFAPRSTV LYLGDTRGKH-SLFEEEI (SEQ ID NO:6). Using these two amino acid sequences, converging sets of degenerate and non-degenerate primers were designed to PCR the beginning of the sbfIR gene from chromosomal DNA.

Two sets primers were synthesized with the following sequences:

5'atgaactccgacggcatcgac3' sbfN-1

(SEQ ID NO:7)

5'aanacyaartcnaccat3' sbf45a (SEQ ID NO:8)

5'atgaacagcgacggcatcgac3' sbfN-1b (SEQ ID NO:9)

5'aasaccaactcctcsaccat3' sbf45a-2

(SEQ ID NO:10)

The primers were used in two separate PCR reactions: sbfN-1+sbf45a, sbfN-1b+sbf45a-2. PCR conditions were 95° C. for 5 min, 1 cycle; 95° C. for 1 min, 54° C. for 1 min, 72° C. 1 min for 25 cycles with Deep Vent® DNA polymerase. The PCR of SbfI chromosomal DNA with the above primers generated ~550 bp DNA fragment. The PCR fragments were gel purified, phenol-$CH_3Cl$ extracted and isopropanol precipitated. The resuspended PCR fragment was blunt-end ligated into pCAB16 at the BsaAI site followed by transformation into E. coli ER2502. pCAB16 clones with PCR inserts were sequenced using the following sequencing primers:

5'ggagccatacagagagcgatttattcg3' 167

(SEQ ID NO:11)

5'ttgaaatcgaattaataagtctggatg3' 168

(SEQ ID NO:12)

DNA sequencing identified an open reading frame (ORF) of 555 bp DNA fragment containing the 5' end of the sbfIR gene.

5. Inverse PCR amplification of DNA downstream of the 5' end SbfI endonuclease gene After identification of the N-terminus of the endonuclease gene, efforts were made to clone adjacent downstream DNA. DNA sequence at the N-terminus of the sbfIR gene was used as the template for primer design.

Four primers were synthesized:

5'ccagtccatgatcttctgaacgcc3' 5B (SEQ ID NO:13)

5'cttcggcagtgggttgataatggc3' 3B (SEQ ID NO:14)

5'agggagatcgacagagatcatcgc3' 5C (SEQ ID NO: 15)

5'tactgcgcgggcgctgctaaagcg3' 3A (SEQ ID NO:16)

As a positive control, converging primers 3A and 5C, were used on SbfI chromosomal DNA. For the inverse PCR, genomic DNA was individually digested with BstBI, BstUI, DraI, HincII, HpyCH4IV, RsaI and ScaI. The digestions were inactivated at 65° C. for 20 min. Self-ligation was set up at a low DNA concentration at 2 μg/ml overnight at 17° C. The resulting circular DNA preps were used as the templates for inverse PCR. PCR conditions were 95° C. for 5 min, 1 cycle; 95° C. for 1 min, 62° C. for 1 min, 72° C. for 2 min for 25 cycles. Converging primers 3A and 5C generated the sbfIR ~400 bp control fragment. Inverse PCR products were found in the HincII and HpyCH4IV templates. The PCR products were gel-purified, phenol/$CH_3Cl$-extracted and isopropanol-precipitated. Immediately downstream of the 3B primer within the sbfIR N-terminus is an ApoI site. This ApoI site was used to digest the inverse PCR products at this site, followed by overnight ligation into EcoRI- and HincII- digested pUC19. The ligated DNA was transferred into ER2502 and ER2683 by transformation. Plasmids were identified that contained the inverse PCR fragment and sequenced directly with pUC19 universal primers 1233 and 1224. Using this DNA sequence, another direct PCR was done with 3B and a newly designed converging primer Sb-3 having the following sequence;

5'gcggcaaccttcatccgg3' Sb-3

(SEQ ID NO:17)

PCR conditions were 95° C. for 5 min, 1 cycle; 95° C. for 1 min, 54° C. for 1 min, 72° C. for 2 min for 25 cycles. A PCR fragment containing ~1200 bp of the C-terminal end of sbfIR and downstream DNA was purified by phenol/CH3Cl -extraction and isopropanol precipitation. The PCR fragment was digested with ApoI and ligated into EcoRI- and HincII- digested pUC19. The ligated DNA was transformed into ER2683 and plasmid DNA was purified. Plasmids containing the PCR fragment were sequenced with pUC19 universal primers 1233 and 1224. After cloning, then sequencing, an ORF with 969 bp long was found. This gene was judged likely to be the sbfIR restriction gene coding for SbfI endonuclease as predicted by N-terminal R.SbfI amino acid protein sequence. An additional ~700 bp of sequenced SbfI chromosomal DNA that was downstream of sbfIR did not appear to contain the SbfI methylase gene.

6. PCR amplification of DNA upstream of SbfI endonuclease

After failing to identify the sbfIM gene downstream of the endonuclease gene, efforts were made to clone adjacent DNA upstream to sbfIR. A PCR reaction was done on the original pUC19 primary libraries of Sau3AI, Bc/I, BstYI, Bg/II, XbaI and NheI to check for the presence of sbfIR using converging primers 5C and 3A:

5'agggagatcgacagagatcatcgc3' 5C (SEQ ID NO:18)

5'tactgcgcgggcgctgctaaagcg3' 3A (SEQ ID NO:19)

PCR conditions were 95° C. for 5 min, 1 cycle; 95° C. for 1 min, 62° C. for 1 min, 72° C. for 2 min for 25 cycles. All libraries, except the XbaI library, contained the ~400 bp sbfIR fragment that should be generated by these two primers from sbfIR DNA sequence. Two separate PCR reactions were done with pUC19 universal primers 1233 and 1224 with primer 5B, in the direction of 5' end of sbfIR, to determine if some of these pUC19 libraries might contain DNA upstream of the sequence sbfIR, perhaps containing the SbfI methylase gene. The libraries tested were the Bg/II, Bc/I and Sau3AI pUC19 libraries. The PCR primers have the following sequence:

5'agcggataacaatttcacacagga3' 1233 pUC19 Universal primer
(SEQ ID NO: 20)
5'cgccagggttttcccagtcacgac3' 1224 pUC19 Universal primer
(SEQ ID NO:21)
5'ccagtccatgatcttctgaacgcc3' 5B
(SEQ ID NO:22)

PCR conditions were 95° C. for 5 min, 1 cycle; 95° C. for 1 min, 62° C. for 1 min, 72° C. for 8 min for 25 cycles. The 1233 and 5B PCR primers generated a predominant fragment of ~1.6 kb for Bg/II and Sau3AI libraries; and ~4.0 kb fragment from the Bc/I library, both perhaps large enough to contain the whole SbfI methylase gene (sbfIM). The PCR products were gel-purified, phenol-CH$_3$Cl extracted and isopropanol precipitated, followed by direct sequencing of the PCR products. Only the PCR fragment from the SbfI Sau3AI-pUC19 partial library generated DNA sequence sufficiently readable to design new PCR primers for a direct PCR of the upstream region in its entirety. The Sau3AI library DNA sequence upstream of the sbfIR gene was used as the template for primer design and a new converging primer 5B-2 was made from sbfIR DNA sequence toward the upstream DNA sequence.

The primers were synthesized with the following sequences:

5'tggggcgaattccagtccatgatcttctgaacgcc3' 5B-2
(underlined nt, EcoRI site) (SEQ ID NO:23)
5'tggggcaagcttgatcaggtccgtg3' S3-1
(underlined nt, HindIII site) (SEQ ID NO:24)
5'tggggcaagcttcgcctgctggttgacc3' S3-2
(underlined nt, HindIII site) (SEQ ID NO:25)
5'tgtggggcaagcttcgccccggtcgtcc3' S3-3
(underlined nt, HindIII site) (SEQ ID NO:26)
5'tggggcaagcttctgcgatccgctgcc3' S3-4
(underlined nt, HindIII site) (SEQ ID NO:27)
5'tggggcaagcttcgttggcggtgctcccgc3' S3-5
(underlined nt, HindIII site) (SEQ ID NO:28)

PCR conditions were 95° C. for 5 min, 1 cycle; 95° C. for 1 min, 54° C. for 1 min, 72° C. for 1 min for 25 cycles. PCR fragments of ~1550 bp were found with both 5B-2+S3-2 or 5B-2+S3-3 primers on SbfI chromosomal DNA. The PCR fragments were gel-purified, phenol-CH$_3$Cl extracted and isopropanol precipitated, followed by EcoRI and HindIII digestion. The digested PCR DNA was heated to 65° C. for 15 min and ligated overnight at 17° C. into EcoRI- and HindIII- digested pUC19. The ligated DNA was transformed into ER2744 and colony PCR was done on 10 colonies of each with universal pUC19 primers 1233 and 1224. PCR conditions were 94° C. for 1 min, 1 cycle; 94° C. for 10 sec, 62° C. for 1 min, 72° C. for 1 min for 25 cycles. Most colonies contained a PCR fragment approximately 1500 bp. Plasmid DNA was purified for 6 clones, 3 for each PCR fragment, by CsCl method and then sequenced using primers 1233 and 1224. DNA sequence was only obtained from clone #5 which contained the PCR fragment generated by primers 5B-2+S3-3. Clone #5 contained a HindIII to EcoRI fragment of ~1200 bp, slightly less then the original PCR fragment. The entire fragment was sequenced with seven additional primers. The sequencing primers have the following sequences:

5'gagcaatgtcacagcgctacggac3' (51)
(SEQ ID NO:29)
5'gatccaacacagtcgagttcaacc3' (52)
(SEQ ID NO:30)
5'aacggcaaacggcgaaagaggacc3' (53)
(SEQ ID NO:31)
5'cctcatgctttggttgaactcgac3' (54)
(SEQ ID NO:32)
5'tcgttgctttcagtgtgaggccgc3' (55)
(SEQ ID NO:33)
5'cgttgtgcccatggtttatcagtc3' (56)
(SEQ ID NO:34)
5'ctcttgctttaccttcgtgtccgc3' (57)
(SEQ ID NO:35)

After sequencing about 1.2 kb, a truncated ORF of 1040 bp long was found upstream of the sbfIR gene. This sequence most likely encoded the 3' end of the SbfI methylase gene. When the amino acid sequence of this ORF was compared to the known gene products in GenBank using BLAST, it showed very high homology to N6-methyl adenine methyltransferases especially those belonging to the PstI recognition family. The sbfIM transcriptional (TGA) stop codon was found to overlap the (GTG) start codon for the SbfI endonulease gene (sbfIR). DNA sequencing across the junction revealed that along with the GTG start, an additional amino acid, serine (S) is present making R.SbfI one amino acid longer than predicted from N-terminal amino acid. The original incorrect sequence is (MN) SDGIDGTVAS IDTARALLKRFGFDAQRYNV (SEQ ID NO:36). In fact R.SbfI is actually 323 amino acids in length, not 322 amino acids, and the N-terminal sequence is: MNSSDGIDGTVASIDTARALLKRFGFDAQ RYNV (SEQ ID NO:37). With the additional Serine, the full SbfI endonuclease gene (sbfIR) is 971 bp. DNA sequencing of #5 also revealed an unknown HindIII site within sbfIM which shortened the original 5B-2+S3-3 PCR fragment. DNA between the S3-3 primer to this HindIII site was lost during cloning.

7. Inverse PCR amplification of DNA upstream of SbfI endonuclease and identification of SbfI methylase After identification of the truncated methylase gene, efforts were made to clone adjacent DNA encoding the 5' end of sbfIM using inverse PCR. Using this sbfIM DNA sequence new primers were designed having the following sequence:

5'ggccacgtaaacgttcggtacatc3' (A1)
(SEQ ID NO:38)
5'tcatttcgctcaaagagcaggggc3' (B1)
(SEQ ID NO:39)

The genomic DNA was digested with HincII in appropriate restriction buffer and inactivated at 65° C. for 20 min. Self-ligation was set up at a low DNA concentration at 2 µg/ml overnight at 17° C. The circular DNA product was used as the template for inverse PCR. PCR conditions were 94° C. for 5 min, 1 cycle; 94° C. for 30 sec, 62° C. for 1 min, 72° C. for 1 min for 25 cycles. The PCR fragment was gel purified from an agarose gel, phenol/CH$_3$Cl-extracted and isopropanol precipitated. The resuspended PCR fragment was blunt-end ligated at 17° C. overnight into pCAB16 digested at the BsaAI site followed by tranformation into ER2502 *E. Coli* cells. Plasmid DNA was purified from twelve colonies. Ten appeared to contain the PCR DNA fragment. Four clones were sequenced directly with the following primers:

5'ggagccatacagagagcgatttattcg3' 167

(SEQ ID NO:40)

5'ttgaaatcgaattaataagtctggatg3' 168

(SEQ ID NO:41)

DNA sequencing identified an open reading frame (ORF) of 495 bp DNA fragment containing the 5' end of sbfIM. The combined DNA sequence upstream of the sbfIR gene revealed the total SbfI methylase gene (sbfIM). The sbfIM gene is 1460 bp which encodes a translated SbfI methylase of 486 amino acids. Transcription of M and R genes is oriented in the same direction. They are arranged in head-to-tail fashion (FIG. 1).

EXAMPLE 2

Expression of SbfIR Gene in *E. coli*

Since the preferred methylase selection method failed to yield a SbfI methylase gene, efforts were made initially to clone the sbfIR gene in a M.PstI pre-modified *E. coli* strain in order to establish an sbfIR clone with the correct DNA sequence. The pstIM gene was first amplified from pBEA-14 plasmid containing the PstI methylase (provided by Bill Jack and Lucia Greenough, New England Biolabs (Beverly, Mass.)). The pstIM gene was cloned into a low copy number plasmid pACYC184 with p15A origin and $Cm^R$ selection marker. The PCR primers have the following sequences:

5'ttccgggatccggaggtttaaaatat-gactaagcggcaacacaataccatatctc3'

(Pst5M, underlined nt, BamHI site) (SEQ ID NO:42)

5'ttgccgcatgcgtcgttacattagctgcaaactctgattgattatttc3'

(Pst3M, underlined nt, SphI site) (SEQ ID NO:43)

PCR conditions were 95° C. for 5 min, 1 cycle; 95° C. for 1 min, 54° C. for 1 min, 72° C. 1 min for 25 cycles with Deep Vent® DNA polymerase. The PCR product was phenol-CH$_3$Cl extracted and isopropanol precipitated, followed by BamHI and SphI digestion overnight at 37° C. Digested DNA was ligated to pACYC184 with compatible ends. Following ligation overnight, the DNA was transferred into ER2744 by transformation. After screening 10 plasmids isolated from individual $Cm^R$ (33 mg/ml) transformants, one clone pACYC184-PstIM #4 contained the correct pstIM fragment as shown by BamHI and SphI digestion. ER2744 [pACYC184-PstIM #4] was made competent by CaCl$_2$ method. The premodified host ER2744 [pACYC184-PstIM] was used for establishing of the SbfI endonuclease.

Two PCR primers were synthesized for PCR amplification of the sbfIR gene.

5'tggctgcagggatccggaggtt-taaaatatgaacagcagtgacggcatcgacggaa cggtagc3'

(sbf5R-2, underlined nt, BamHI site) (SEQ ID NO:44)

5'tcgggccccgggctcgagtctaacgttcgtacggcccaagaaatctagacc3'

(sbf3RT7, underlined nt, XhoI site) (SEQ ID. NO:45)

PCR conditions were 95° C. 5 min, 1 cycle; 95° C. for 1 min, 54° C. for 1 min, 72° C. for 1 min for 25 cycles with Deep Vent® DNA polymerase. PCR DNA containing the sbfIR gene was amplified from genomic DNA and purified by phenol/ CH$_3$Cl -extraction and CH$_3$Cl extraction, precipitated with isopropanol, dried and resuspended in TE buffer. The PCR DNA was blunt-end ligated to pCAB16 at the BsaAI site. The ligated DNA was transformed into M.PstI pre-modified *E. coli* ER2744 [pACYC184-PstIM] and $Ap^R$ $Cm^R$ transformants were selected at 37° C. [$Ap^R$ $Cm^R$ :(100 mg/ml) and (33 mg/ml]. After screening 12 plasmids, 4 clones were found to contain inserts. 500 ml LB+Amp cultures of clones #1 and #7 were grown overnight at 37° C. Plasmid DNA was purified from 450 ml of each cell culture by the CsCl method, and the other 50 ml of the cells of each were harvested by centrifugation and resuspended in 2 ml sonication buffer (10 mM Tris-HCl, pH 8, 0.1 mM EDTA, 50 mM NaCl, 1 mM β-mercaptoethanol). Cells were lysed by sonication and cell debris removed by centrifugation. Cell lysate was assayed on 1 DNA for SbfI activity. No SbfI activity was detected for either pCAB16-SbfIR #1 or #7 clones. Both pCAB16-SbfIR clones were sequenced directly with the following primers:

5'ggagccatacagagagcgatttattcg3' 167

(SEQ ID NO:46)

5'ttgaaatcgaattaataagtctggatg3' 168

(SEQ ID NO:47)

DNA sequence showed an intact sbfIR in the opposite orientation to Plac and mspIR. The pCAB16-sbfIR #1 and #7 clones contained correct DNA sequence for sbfIR, so an attempt was made to subclone the SbfI endonuclease gene from pCAB16-sbfIR #1 and #7 into pLT7K, and then transform into ER2744 [pACYC184-PstIM]. Using the flanking BamHI and XhoI sites designed within the PCR primers, 10 μg of each pCAB16-sbfIR plasmid was digested with BamHI and XhoI at 37° C. for 2 hours and the sbfIR fragment were gel purified from a agarose gel, phenol-CH$_3$Cl extracted and isopropanol precipitated. The resuspended PCR fragment was ligated at 17° C. overnight into pLT7K with compatible ends, followed by transformation into ER2744 [pACYC184-PstIM] and plated on $Ap^R$ $Cm^R$ plates at 37° C. Plasmid DNA's were purified from 18 colonies (9 each from gel pure pCAB16-sbfIR #1 and #7, respectfully), 6 clones were found to carry the PCR insert. pLT7K-SbfIR #5, #12 and #14 were inoculated into pre-warmed 10 ml cultures containing LB+$Ap^R$ $Cm^R$ and grown at 37° C. overnight without shaking. 2 ml of the overnight cultures were diluted in pre-warmed 50 ml cultures containing LB+$Ap^R$ $Cm^R$ and grown at 37° C. to an OD590 of between 0.8 and 1.0, IPTG was to added to 85 mg/L and induced at 30° C. for ~2 hours. Cells were harvested and lysed by sonication. Clarified cell lysates were assayed for SbfI activity on 1 DNA. The extracts generated partial SbfI digestion pattern. pLT7K-SbfIR #12 was sequenced with the following primers:

5'tactgcgcgggcgctgctaaagcg3' 3A (SEQ ID NO:48)

5'aatttctgctctcgcctgccgggc3' 3C (SEQ ID NO:49)

5'ccagtccatgatcttctgaacgcc3' 5B (SEQ ID NO:50)

5'agggagatcgacagagatcatcgc3' 5C (SEQ ID NO:51)

The DNA sequence of pLT7K-SbfIR #12 showed that it carried an intact sbfIR gene. Shortly after this result, the SbfI methylase gene (sbfIM) was completely identified by inverse PCR and sequenced. A final strategy was employed in which the sbfIM gene was expressed from a low-copy-number plasmid and the endonuclease gene from pLT7K-SbfIR #12 was then transferred into this SbfI pre-modified *E. coli* host. The sbfIM gene was first amplified from genomic DNA in a PCR reaction and was cloned into a low copy number plasmid pACYC184 with p15A origin and $Cm^R$ selection marker. The PCR primers have the following sequences:

5'tggccgggatccggaggtttaaaatatgcatccgatcgccagcactgaaactcgccgc3'

(sbf5M, underlined nt, BamHI site) (SEQ ID NO:52)

5'ttgccgcatgcctcacgaggcagattccggaatctcacagaagagtc3'

(sbf3M, underlined nt, SphI site) (SEQ ID NO:53)

PCR conditions were 95° C. 5 min, 1 cycle; 95° C. for 1 min, 54° C. for 1 min, 72° C. for 1 min for 30 cycles with Deep Vent® DNA polymerase. PCR DNA containing the sbfIM gene was amplified from genomic DNA and purified by phenol/CH3Cl -extraction, precipitated with isopropanol, dried and resuspended in TE buffer. The PCR DNA was blunt-end ligated to pCAB16 at the BsaAI site. The ligated DNA was transformed into ER2502 and Cm$^R$ transformants were selected at 37° C. After screening 12 plasmids, two pCAB16-sbfIM clones, #3 and #5 were completely sequenced with the following primers:

5'ggagccatacagagagcgatttattcg3' 167

(SEQ ID NO:54)

5'ttgaaatcgaattaataagtctggatg3' 168

(SEQ ID NO:55)

5'ctttcccgtacttacaccgatgcc3' sbf- M1

(SEQ ID NO:56)

5'tcctcgatcttgggcgaacgggcc3' sbf-M2

(SEQ ID NO:57)

DNA sequence showed an intact sbfIM in both orientations to Plac and mspIR. The pCAB16-sbfIR #3 and #5 clones contained correct DNA sequence for the sbfIM gene, so an attempt was made to subclone the SbfI methylase gene from pCAB16-sbfIR #3 and #7 into the low copy number plasmid pACYC184 with p15A origin and Cm$^R$ selection marker. Using the flanking BamHI and SphI sites designed within the PCR primers, 5 μg of each pCAB16-SbfIM plasmid was digested with BamHI and SphI at 37° C. for 2 hours and the sbfIM fragment were gel purified from a agarose gel and combined, phenol-CH$_3$Cl extracted and isopropanol precipitated. The re-suspended PCR fragment was was ligated at 17° C. overnight into pACYC184 with compatible ends, followed by transformation into ER2848 and then selected for Cm$^R$ transformants. Plasmid DNA was purified from 8 colonies and PCR was done on two clones, #6 and #7, with primers sbf5M and sbf3M. PCR conditions were 95° C. 5 min, 1 cycle; 95° C. for 1 min, 54° C. for 1 min, 72° C. for 1 min for 25 cycles with Deep Vent® DNA polymerase. pACYC184-SbfIM #6 and #7 contained the correct size insert for sbfIM.

The plasmid pACYC184-SbfIM #7 was transferred into ER2848 to premodify E. coli. Competent cells were made by CaCl$_2$ method and the final strategy was employed in which the sbfIM gene was expressed from a low-copy-number plasmid [pACYC184-SbfIM] and the endonuclease gene from [pLT7K-SbfIR]. Isolate pLT7K-SbfIR #12 was transferred into ER2848 [pACYC184-SbfIM] and plated on Ap$^R$ Cm$^R$ plates at 37° C. overnight. Two individual colonies were inoculated into 10 ml LB+Ap$^R$ Cm$^R$ and grown at 37° C. overnight. 1 ml of each overnight culture was inoculated into 50 ml of LB+Ap$^R$ Cm$^R$ and grown at 37° C. to OD590 0.8 to 1.0, then the culture temperature was then lowered to 30° C., followed by IPTG (85 mg/L) induction at 30° C. for 2 hours to overnight. Both individual clones expressed R.SbfI at more ~10$^5$ units/g of wet E. coli cells (FIG. 8).

The strain NEB#1500, ER2848 [pACYC184-SbfIM #7, pLT7K-SbfIR #12 has been deposited under the terms and conditions of the Budapest Treaty with the American Type Culture Collection on Aug. 5, 2003 and received ATCC Accession No. PTA-5371.

What is claimed is:

1. Isolated DNA encoding the SbfI restriction endonuclease, wherein the isolated DNA is obtainable from *Streptomyces* species Bf-61.

2. A recombinant DNA vector comprising a vector into which a DNA segment encoding the SbfI restriction endonuclease has been inserted.

3. Isolated DNA encoding the SbfI restriction endonuclease and SbfI methylase, wherein the isolated DNA is obtainable from ATCC No. PTA-5371.

4. A vector which comprises the isolated: DNA of claim 3.

5. A host cell transformed by the vector of claim 2 or 4.

6. A method of producing recombinant SbfI restriction endonuclease comprising culturing a host cell transformed with the vector of claim 2 or 4 under conditions suitable for expression of said endonuclease.

* * * * *